(12) United States Patent
Suzuki

(10) Patent No.: US 10,688,550 B2
(45) Date of Patent: Jun. 23, 2020

(54) MOLD FOR USE IN PRODUCING IN-VIVO INDWELLING MEMBER AND METHOD FOR PRODUCING IN-VIVO INDWELLING MEMBER BY USING SAID MOLD

(71) Applicant: KANEKA CORPORATION, Osaka-shi, Osaka (JP)

(72) Inventor: Shohei Suzuki, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 442 days.

(21) Appl. No.: 15/548,990

(22) PCT Filed: Jan. 29, 2016

(86) PCT No.: PCT/JP2016/052685
§ 371 (c)(1),
(2) Date: Aug. 4, 2017

(87) PCT Pub. No.: WO2016/125704
PCT Pub. Date: Aug. 11, 2016

(65) Prior Publication Data
US 2018/0021834 A1    Jan. 25, 2018

(30) Foreign Application Priority Data

Feb. 6, 2015  (JP) .................................. 2015-022537

(51) Int. Cl.
*B21D 22/06* (2006.01)
*A61B 17/12* (2006.01)
*A61B 17/00* (2006.01)

(52) U.S. Cl.
CPC ........ *B21D 22/06* (2013.01); *A61B 17/12113* (2013.01); *A61B 17/12145* (2013.01); *A61B 2017/00526* (2013.01)

(58) Field of Classification Search
CPC ........ A61B 17/12113; A61B 17/12145; A61B 17/1214; A61B 17/1215; A61B 17/12154;
(Continued)

(56) References Cited

U.S. PATENT DOCUMENTS 4,619,025 A * 10/1986 McManus .............. B21D 11/06
165/172
5,749,891 A *  5/1998 Ken .................. A61B 17/12022
606/200
(Continued)

FOREIGN PATENT DOCUMENTS

EP    0 747 014 A1   12/1996
EP    0 765 636 A2    4/1997
(Continued)

OTHER PUBLICATIONS

International Search Report, issued in PCT/JP2016/052685, dated Mar. 22, 2016.
(Continued)

*Primary Examiner* — Adam J Eiseman
*Assistant Examiner* — Bobby Yeonjin Kim
(74) *Attorney, Agent, or Firm* — Birch, Stewart, Kolasch & Birch, LLP

(57) ABSTRACT

A mold for use in producing an in-vivo indwelling member having a linear primary coil formed in a three-dimensional shape includes a transformable member transformable between an assembled state and an unfolded state, the transformable member has, in the assembled state, an outer portion that is arranged at an outer side and an inner portion that is arranged at an inner side of the outer portion, with being connected to the outer portion, and the outer portion and the inner portion have holding portions for holding the primary coil. The mold makes it possible to easily produce an in-vivo indwelling member having a three-dimensional
(Continued)

shape that allows the in-vivo indwelling member to be stably arranged within a bulge such as an aneurysm.

9 Claims, 25 Drawing Sheets

(58) Field of Classification Search
CPC .............................. A61B 2017/00526; A61B 2017/12054–12095; B21F 45/008; B21F 3/00; B21F 3/02; A61F 2002/077; A61F 2002/823; B21D 11/06; B21D 11/07
USPC ............................................ 269/266, 71, 58
See application file for complete search history.

(56) References Cited

U.S. PATENT DOCUMENTS

| | | | | |
|---|---|---|---|---|
| 7,879,064 B2* | 2/2011 | Monstadt | ......... | A61B 17/12022 606/200 |
| 8,801,747 B2* | 8/2014 | Strauss | ............ | A61B 17/12022 606/200 |
| 2003/0019270 A1* | 1/2003 | Kobayashi | ............. | B21D 11/07 72/154 |
| 2008/0319532 A1 | 12/2008 | Monstadt et al. | | |
| 2015/0238200 A1* | 8/2015 | Garza | ............... | A61B 17/00234 606/200 |

FOREIGN PATENT DOCUMENTS

| | | |
|---|---|---|
| JP | 9-99094 A | 4/1997 |
| JP | WO 99/09893 A1 | 3/1999 |
| JP | 3024071 B2 | 3/2000 |
| JP | 2001-513389 A | 9/2001 |
| JP | 2004-511293 A | 4/2004 |
| WO | WO 02/32325 A1 | 4/2002 |

OTHER PUBLICATIONS

Written Opinion of the International Searching Authority, issued in PCT/JP2016/052685, dated Mar. 22, 2016.

* cited by examiner

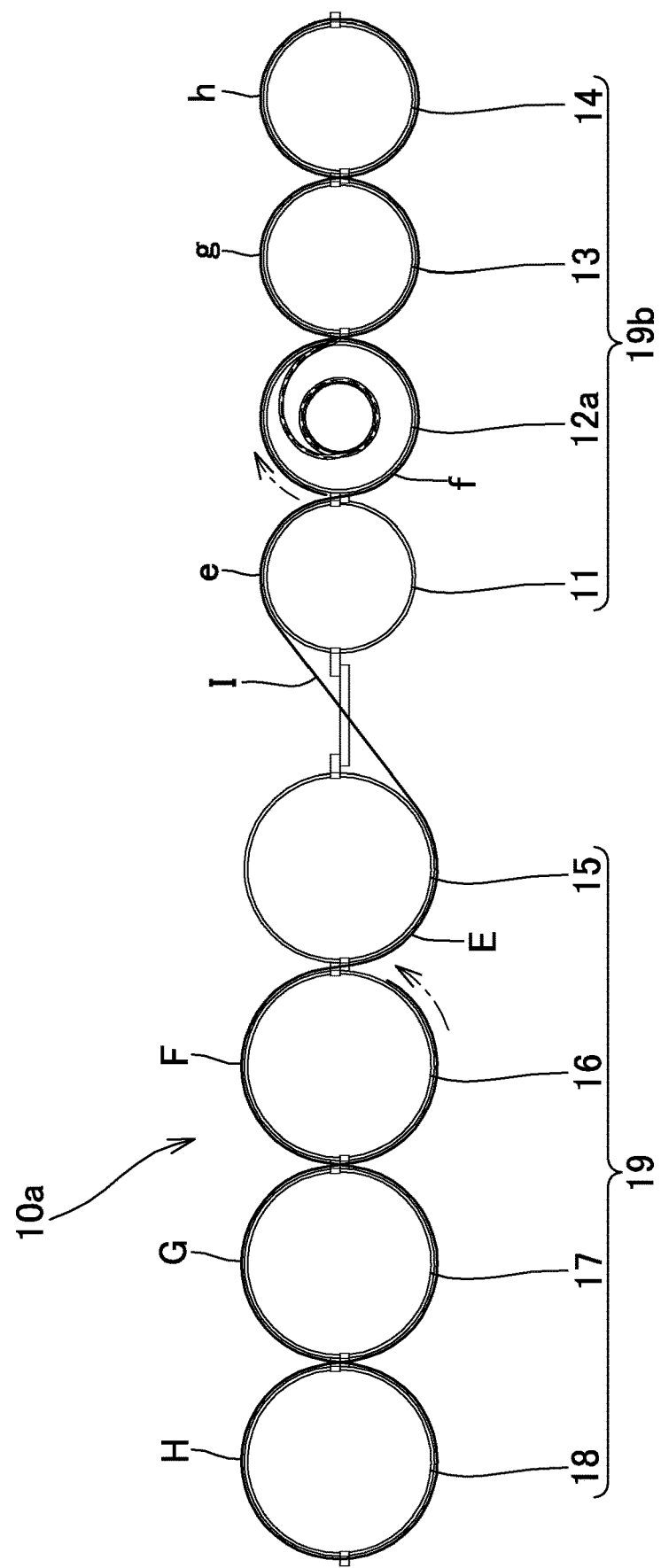

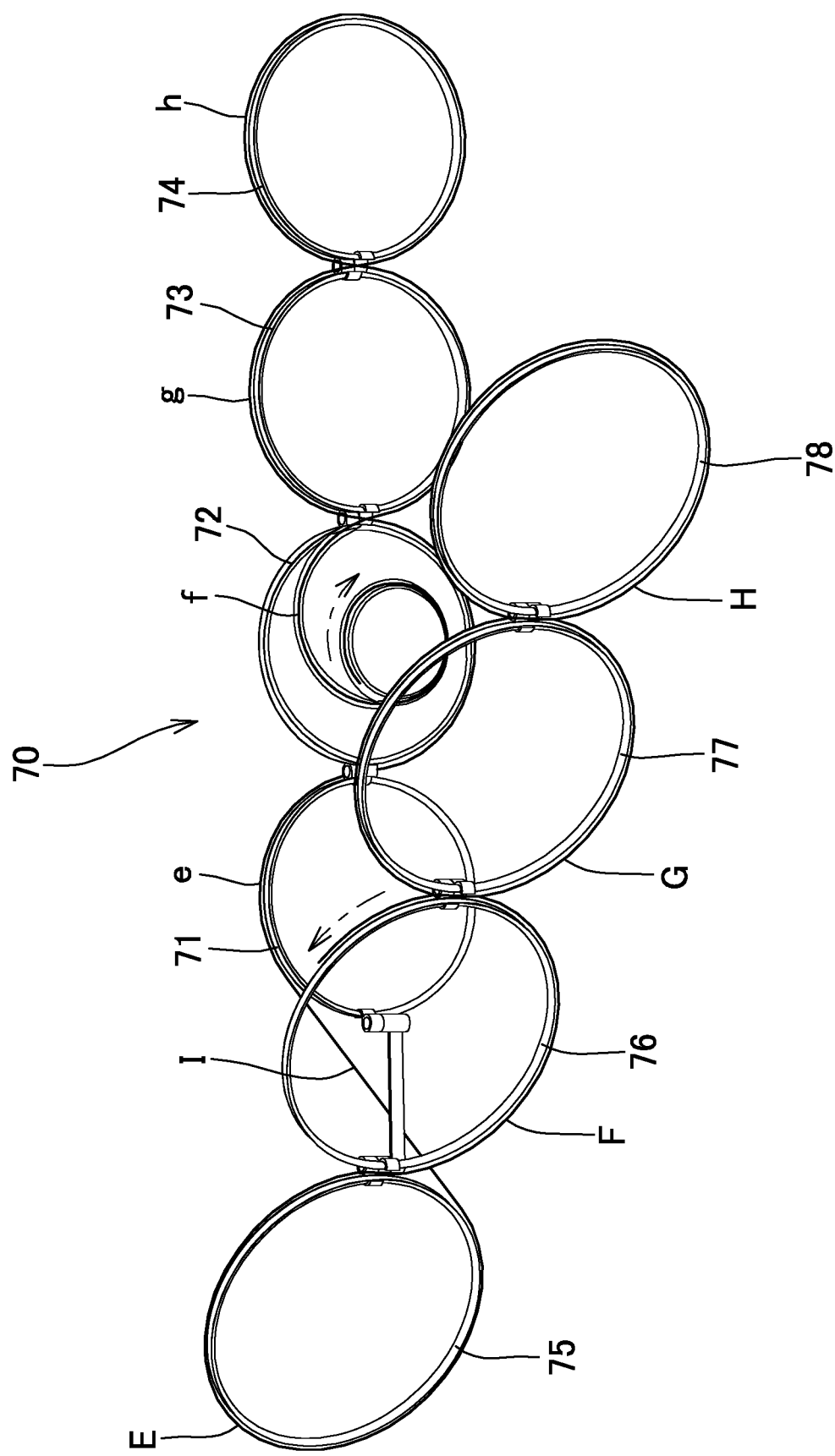

MOLD FOR USE IN PRODUCING IN-VIVO INDWELLING MEMBER AND METHOD FOR PRODUCING IN-VIVO INDWELLING MEMBER BY USING SAID MOLD

TECHNICAL FIELD

One or more embodiments of the present invention relates to a mold for use in producing an in-vivo indwelling member having a primary coil formed in a three-dimensional shape, and a method for producing an in-vivo indwelling member by using the mold.

BACKGROUND ART

Examples of a method for treating a bulge such as an aneurysm formed in a blood vessel include a method in which an in-vivo indwelling member such as an embolus material is inserted into a bulge. By such a treatment, a thrombus can be formed around the embolus material within the bulge to reduce the risk of rupture of the bulge. To insert an embolus material into a desired bulge, first, a medical instrument called microcatheter which includes an elongated tube having a small diameter is inserted into a blood vessel and guided to the bulge such as an aneurysm. Then, the embolus material is inserted into the bulge through the inner cavity of the tube of the microcatheter and indwelled therein.

As such an embolus material, a material has been widely used which is prepared by shaping a metal wire into a coil shape to form a linear primary coil, followed by further shaping the linear primary coil into a helical shape to form a secondary coil. In guiding the embolus material to a bulge such as an aneurysm, the shape of the embolus material is made straight in the thin tube of the microcatheter. When the embolus material is released from the tube within the bulge, the shape returns to the original shape of the secondary coil, and the embolus material can remain within the bulge. A coil referred to as the secondary coil is obtained by imparting a secondary shape that is a three-dimensional shape to a linear primary coil.

Meanwhile, examples of the shape of a bulge include a spherical shape, an elliptical spherical shape, and a two-bulge shape, and a shape in which another blood vessel branches from a bulge. Among them, one of bulge types called a wide-neck aneurysm which has a wide boundary with respect to a parent blood vessel, relative to the diameter of the aneurysm, may cause a serious risk, as follows. A helical secondary coil, for example, having a uniform diameter in the axial direction thereof may be used in indwelling a secondary coil within the bulge. The shape of the secondary coil to be used is cylindrical and does not sufficiently correspond to the shape of the inner wall surface of the bulge, and the neck opening is wide. With this, the pressing force of the secondary coil against the inner wall surface of the bulge is reduced, thereby avoiding the secondary coil from remaining within the bulge, even when the shape of the secondary coil returns to the original coil shape within the bulge. This causes the secondary coil to protrude to the parent blood vessel and to be flown to the periphery by the blood flow.

For such a wide-neck aneurysm, the secondary coil may have a shape that is not helical as described above but is a complicated three-dimensional structure, which is different from a helical shape, and partially fits the shape of the inner wall surface of the bulge. This allows the secondary coil to return to the three-dimensional structure within the bulge so as to apply pressing force to the inner wall surface of the bulge. Accordingly, the secondary coil is firmly fixed, resulting in a reduction in the possibility that the secondary coil protrudes to the parent blood vessel.

Regarding the secondary coil having such a complicated three-dimensional structure different from a helical shape, various production methods therefor have already been disclosed. For example, Patent Literature 1 discloses a method for producing a secondary coil having a three-dimensional structure by winding a primary coil around a core having a mandrel shape (with a pin), a clover shape, or a cubic shape. However, when the primary coil is wound around the core as described above to form a complicated three-dimensional structure in which the primary coil may be damaged upon being wound in the production process, it is necessary to pay attention to the order of winding of the primary coil. This causes the work to be complicated.

In addition, Patent Literature 2 also discloses a method for producing a secondary coil having a three-dimensional structure by winding a coil around a core, such as a rod, a cube, and a core with a groove. Similarly to the case of the method disclosed in Patent Literature 1, this method has problems in damaging a primary coil upon winding, and in workability.

Meanwhile, Patent Literature 3 discloses, in addition to a method in which a primary coil is wound around a core or the like, a method for producing a secondary coil having a spherical three-dimensional structure by inserting a primary coil into a spherical mold. In the method using a mold, a spherical internal space is formed by fitting together paired molds each having a hemispherical internal space, and a secondary coil having a spherical three-dimensional structure is formed by inserting a primary coil into the internal space. However, this method has the following problem. As shown in FIG. 27, it is easy to insert a primary coil 1 into an internal space 201 of a mold 200, but movement of the primary coil 1 in the internal space 201 cannot be controlled. Thus, the primary coil 1 is not inserted in a random manner and is made into a general helical shape. In addition, with the general helical shape, the primary coil cannot be arranged in the internal space 201 as intended, and therefore uniform secondary coils cannot be stably shaped.

CITATION LIST

Patent Literature

[PTL 1] Japanese Unexamined Patent Application Publication (translation of PCT application) No. 2001-513389
[PTL 2] Japanese Unexamined Patent Application Publication (translation of PCT application) No. 2004-511293
[PTL 3] Japanese Patent No. 3024071

SUMMARY

One or more embodiments of the present invention has been made in view of the above-described problems of the conventional art, and an object of one or more embodiments of the present invention is to provide: a mold for use in easy production of an in-vivo indwelling member having a three-dimensional shape that allows the in-vivo indwelling member to be stably arranged within a bulge such as an aneurysm; and a method for producing an in-vivo indwelling member by using the mold.

As a result of thorough research, the present inventor has found that the above problems can be solved by using a mold including a transformable member that is transformable between an assembled state and an unfolded state and has, in the assembled state, an outer portion that is arranged at an outer side and an inner portion that is arranged at an inner side of the outer portion with being connected to the outer portion, and thus has achieved the present invention.

One or more embodiments of the present invention is directed to a mold for use in producing an in-vivo indwelling member having a linear primary coil formed in a three-dimensional shape, the mold including a transformable member transformable between an assembled state and an unfolded state, in which the transformable member has, in the assembled state, an outer portion that is arranged at an outer side and an inner portion that is arranged at an inner side of the outer portion, with being connected to the outer portion, and each of the outer portion and the inner portion has a holding portion for holding the primary coil.

In the mold according to an aspect of the present invention, the transformable member may include a plurality of piece members connected to each other. In addition, the plurality of piece members may be connected to each other by a connection portion that allows a relative positional relationship between adjacent piece members to be changed. Furthermore, the plurality of piece members may include at least one piece member that has a loop structure. Moreover, the plurality of piece members may include at least one piece member that is connected to be linear in the unfolded state.

In the mold according to another aspect of the present invention, the outer portion may be provided with a through hole, and the inner portion may be partially located within the through hole in the assembled state.

In the mold according to still another aspect of the present invention, each holding portion may be provided at a peripheral portion of the transformable member. Alternately, the holding portions may be provided in the transformable member so as to face the same side in the unfolded state.

In the mold according to still another aspect of the present invention, the transformable member may have at least one member on which a helical or scroll-shaped holding portion is provided.

Furthermore, one or more embodiments of the present invention is directed to a method for producing an in-vivo indwelling member having a linear primary coil formed in a three-dimensional shape, the method including the steps of: arranging the primary coil on a mold that is in an unfolded state, the mold including a transformable member that is transformable between an assembled state and the unfolded state, and has, in the assembled state, an outer portion arranged at an outer side and an inner portion arranged at an inner side of the outer portion with being connected to the outer portion; and transforming the linear primary coil into a three-dimensional shape by transforming the mold with the primary coil arranged thereon so that the inner portion of the mold is arranged at the inner side of the outer portion of the mold, thereby making the mold into the assembled state.

According to one or more embodiments of the present invention, an in-vivo indwelling member having a three-dimensional shape that allows the in-vivo indwelling member to be stably arranged within a bulge such as an aneurysm, can be easily produced.

BRIEF DESCRIPTION OF THE DRAWINGS

FIG. 23 is an explanatory diagram schematically showing a state in the middle of production of an in-vivo indwelling member by using a modification of the first embodiment of the mold according to one or more embodiments of the present invention.

FIG. 25 is an explanatory diagram schematically showing a state in the middle of production of an in-vivo indwelling member by using a modification of the third embodiment of the mold according to one or more embodiments of the present invention.

DESCRIPTION OF EMBODIMENTS

Figure 1A:
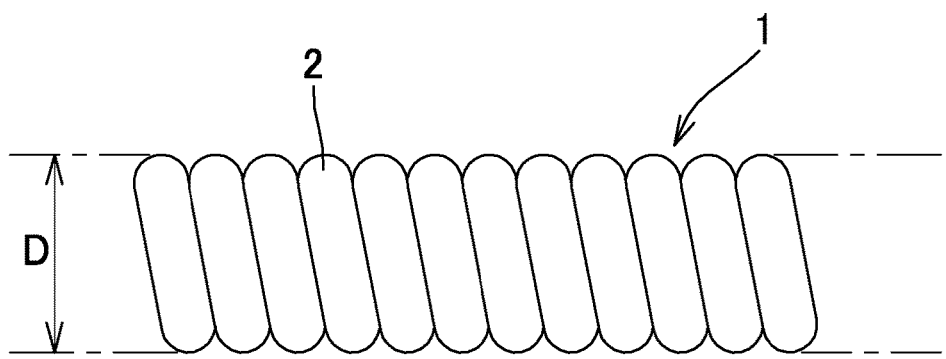
FIG. 1A is a side view showing the outline of an example of an embodiment of a primary coil used in one or more embodiments of the present invention.

Hereinafter, a mold for use in producing an in-vivo indwelling member according to one or more embodiments of the present invention (hereinafter, it may be simply referred to as "mold") and a method for producing an in-vivo indwelling member by using the mold will be described with reference to the drawings. The shape, the material, the size, the length, and the like of each member of in-vivo indwelling members described as embodiments shown in the drawings are described as examples, and can be changed as appropriate. In addition, for the sake of convenience, reference characters are omitted in the drawings in some cases, and in such a case, reference is made to another drawing. Moreover, for the sake of convenience, the dimensions of various members in the drawings are adjusted in some cases so that those members are easily viewed.

In one or more embodiments of the present invention, in producing an in-vivo indwelling member (hereinafter, it may be simply referred to as "secondary coil") by imparting a three-dimensional shape to a primary coil, a linear primary coil is used. The primary coil is formed of a wire. The material of the wire is not particularly limited, and a wire made of a metal can be used. Examples of the metal include platinum, tungsten, gold, tantalum, iridium, titanium, stainless, and an alloy or a superelastic alloy containing a metal arbitrarily selected from these materials. In addition, a cross-sectional shape of the wire is not limited to a circular shape, and various shapes such as an ellipse and a square shape are selectable. Furthermore, in the case where the cross-sectional shape of the wire is a circular shape, the diameter of the cross-sectional shape (the wire diameter) is arbitrarily selectable from a range of about $\phi$ 0.010 mm to 0.200 mm, although it depends on the size of a bulge. In the case where the cross-sectional shape of the wire is not a circular shape, the maximum width of the cross-sectional shape is arbitrarily selectable from a range of about 0.010 mm to 0.200 mm.

Figure 1B:
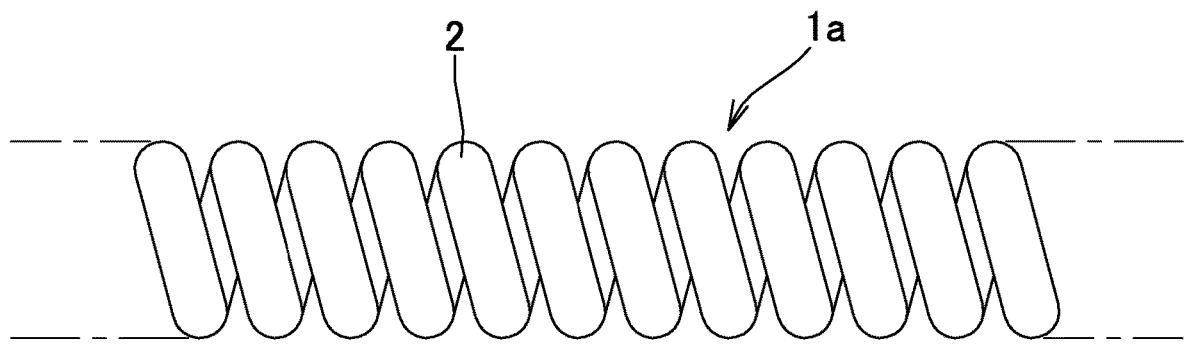
FIG. 1B is a side view showing the outline of another example of the embodiment of the primary coil used in one or more embodiments of the present invention.

The primary coil can be shaped, for example, by winding the above-described wire around a core wire. The inter-wire distance (pitch interval) of the primary coil is not particularly limited. For example, adjacent parts of a wire 2 may be in close contact with each other as in a primary coil 1 shown in FIG. 1A, or a predetermined interval may be provided between adjacent parts of the wire 2 as in a primary coil 1*a* shown in FIG. 1B. The pitch interval may be uniform over the entirety of the primary coil or may be different. In addition, a portion in which parts of the wire are in close contact with each other and a portion in which an interval is provided between adjacent parts of the wire may be combined. The entire shape of the primary coil is not particularly limited as long as it is linear. From the standpoint of easiness of insertion into a shaping groove of a mold described later, the primary coil may be formed, for example, in a straight shape as shown in FIG. 1A and 1B.

Figure 2:
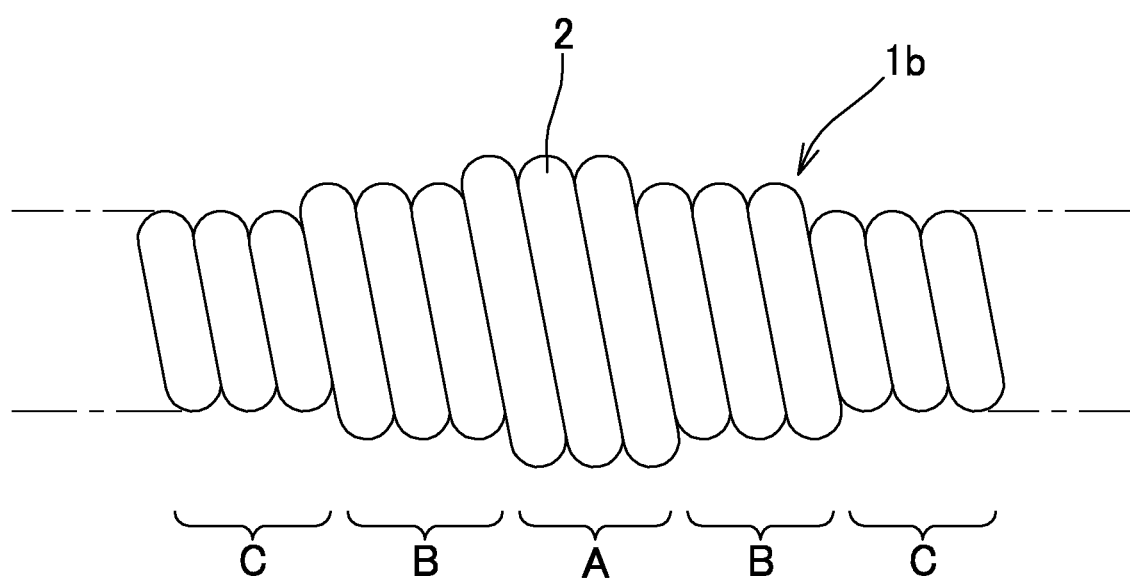
FIG. 2 is a side view showing the outline of still another example of the embodiment of the primary coil used in one or more embodiments of the present invention.

The outer diameter (for example, see reference character D in FIG. 1A) of the primary coil is selectable as appropriate in accordance with the size of the inner cavity of a microcatheter or the like to be used for guiding a finally-obtained in-vivo indwelling member to a bulge. For example, in the case where the microcatheter is designed for 0.010 inches (0.254 mm) to 0.018 inches (0.457 mm), the outer diameter may be $\phi$ 0.200 mm to $\phi$ 0.450 mm. In addition, the outer diameter of the primary coil may be uniform over the overall length of the primary coil (for example, see FIGS. 1A and 1B), or may be changed arbitrarily. For example, in the case where the microcatheter is designed for 0.010 inches to 0.018 inches, the outer diameter may be changed partially within $\phi$ 0.200 mm to $\phi$ 0.450 mm as in a primary coil 1*b* shown in FIG. 2. In the example shown in FIG. 2, the primary coil has a shape in which a part A having the largest outer diameter when the wire 2 is wound, a part B having an outer diameter smaller than that of the part A, and a part C having an outer diameter smaller than that of the part B are sequentially and continuously arranged in order of C, B, A, B, C . . . However, the order of the parts A, B, and C is not limited thereto. In addition, the magnitude of the outer diameter is not limited to three kinds as shown in FIG. 2, and may be two or four or more kinds. The primary coil as shown in FIG. 2 can be produced, for example, by using a core wire that has a stepped or a tapered shape.

In one or more embodiments of the present invention, an extension prevention wire may be provided inside the primary coil. The extension prevention wire may be a single wire or a stranded wire. The material of the extension prevention wire is not particularly limited, and a resin, a metal such as platinum, tungsten, titanium, gold, iridium, palladium, tantalum, alloys of these metals, and stainless steel, or the like can be used. A location at which the primary coil and the extension prevention wire are connected to each other, and a method by which the primary coil and the extension prevention wire are connected to each other are also not particularly limited.

Connection between the extension prevention wire and the primary coil may be made prior to arrangement onto a mold for use in producing an in-vivo indwelling member, or after heat treatment, as described later.

In addition, in one or more embodiments of the present invention, a tip end portion may be provided at an end of the primary coil. The shape of the tip end portion is not particularly limited. For prevention of damage in a blood vessel wall, the tip end portion may have a rounded shape, such as a hemispherical shape or a semielliptical spherical shape. The material forming the tip end portion is not particularly limited, and the materials that are the same as those of the primary coil and the extension prevention wire can be selected as appropriate and used. Moreover, a method for joining the tip end portion is also not particularly limited, and a conventional method can be adopted.

The tip end portion may be joined prior to the arrangement onto the mold for use in producing an in-vivo indwelling member, or after the heat treatment, as described later.

In one or more embodiments of the present invention, an in-vivo indwelling member having a secondary shape with a complicated three-dimensional arrangement different from a helical shape is formed by further shaping the above-described linear primary coil. A predetermined mold is used in shaping the primary coil into such a secondary shape with a three-dimensional arrangement.

The mold according to one or more embodiments of the present invention includes a transformable member that is transformable between an assembled state and an unfolded state. The transformable member has: an outer portion that is arranged at the outer side in the assembled state; and an inner portion that is arranged at the inner side of the outer portion, while being connected to the outer portion, in the assembled state. Each of the outer portion and the inner portion has a holding portion for holding the primary coil.

The transformable member is transformable between the assembled state and the unfolded state as described above, in the unfolded state, so that the primary coil can be easily arranged on the holding portion of the transformable member. In addition, after the primary coil is arranged on the holding portion, the transformable member can be transformed into the assembled state with the primary coil arranged thereon. Therefore, a secondary shape with a three-dimensional arrangement can be easily imparted to the primary coil in accordance with the structure of the transformable member in the assembled state, without winding the primary coil around a core or the like as in the conventional art. In addition, the transformable member is transformable so as to be arranged at the outer side and the inner side in the assembled state. Thus, a three-dimensional arrangement formed by the mold including the transformable member having such a specific structure allows a complicated three-dimensional arrangement to be provided, which is different from a general helical shape as in the conventional art. Thus, it is possible to easily impart, to the primary coil, a secondary shape with a predetermined three-dimensional arrangement that can correspond to the shape of the inner wall surface of the aneurysm, while a space is ensured within a bulge such as a wide-neck aneurysm. Furthermore, since the mold is transformable, the arrangement of the primary coil in the assembled state or in the middle of assembling can easily be checked, and if the arrangement of the primary coil has a problem, the arrangement is easily corrected by returning the mold from the assembled state or from the middle of assembling to the unfolded state.

The mold according to one or more embodiments of the present invention will be described with reference to the drawings.

Figure 3:
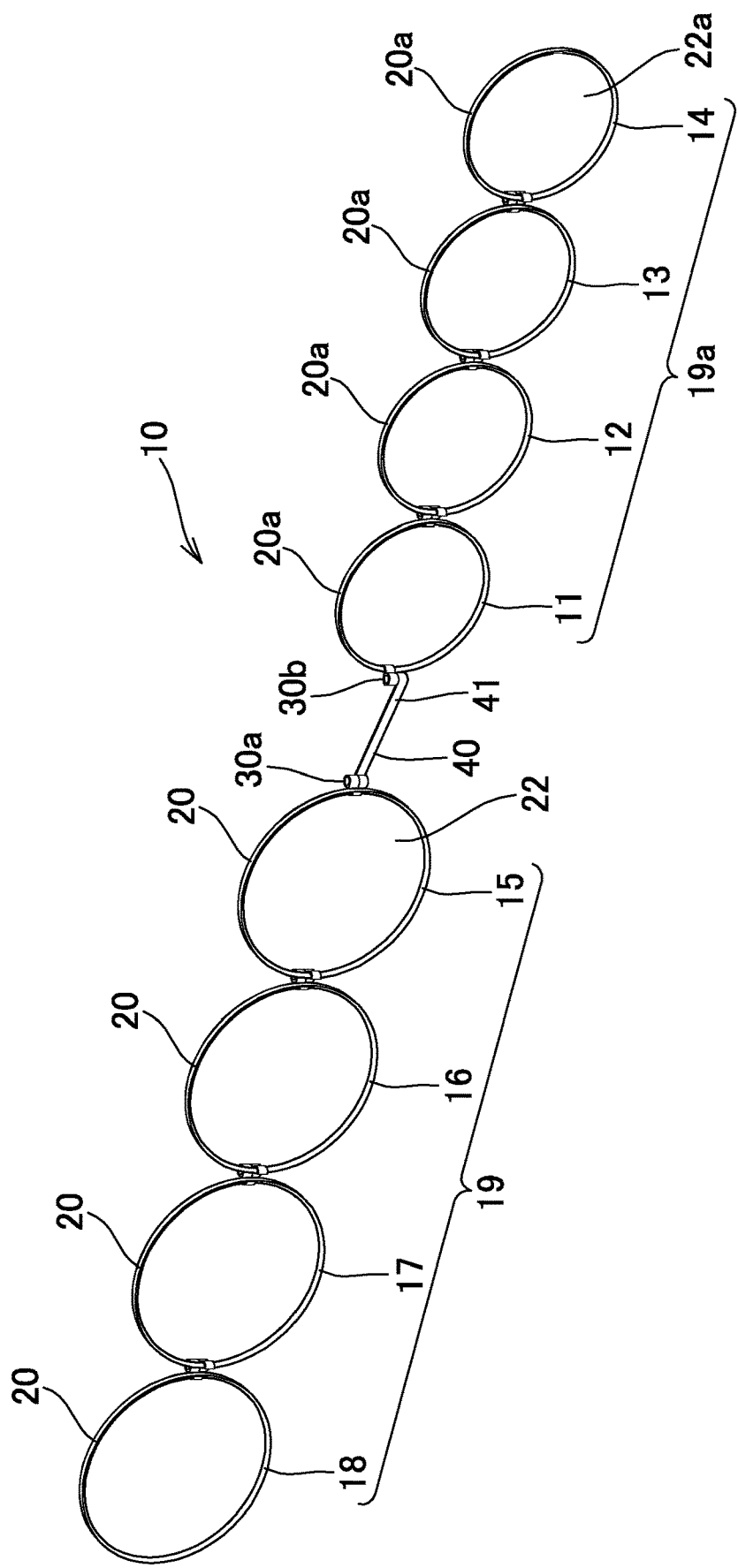
FIG. 3 is a perspective view schematically showing an unfolded state of a first embodiment of a mold according to one or more embodiments of the present invention.
Figure 4:
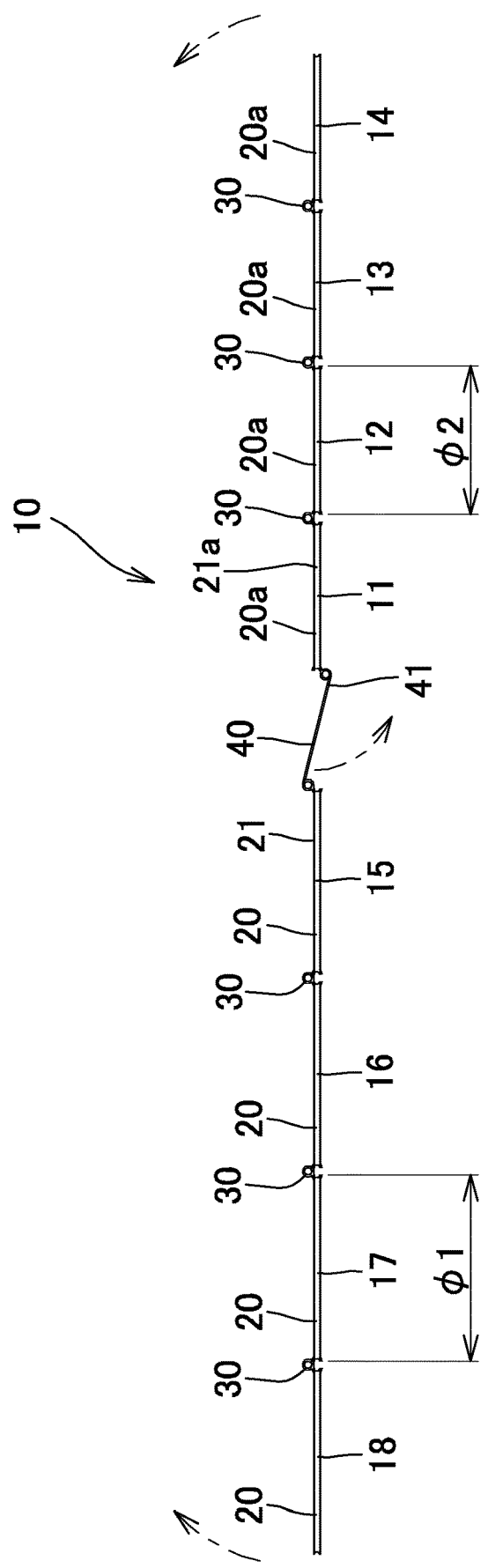
FIG. 4 is a plan view schematically showing the unfolded state of the first embodiment, seen from above of FIG. 3.
Figure 5:
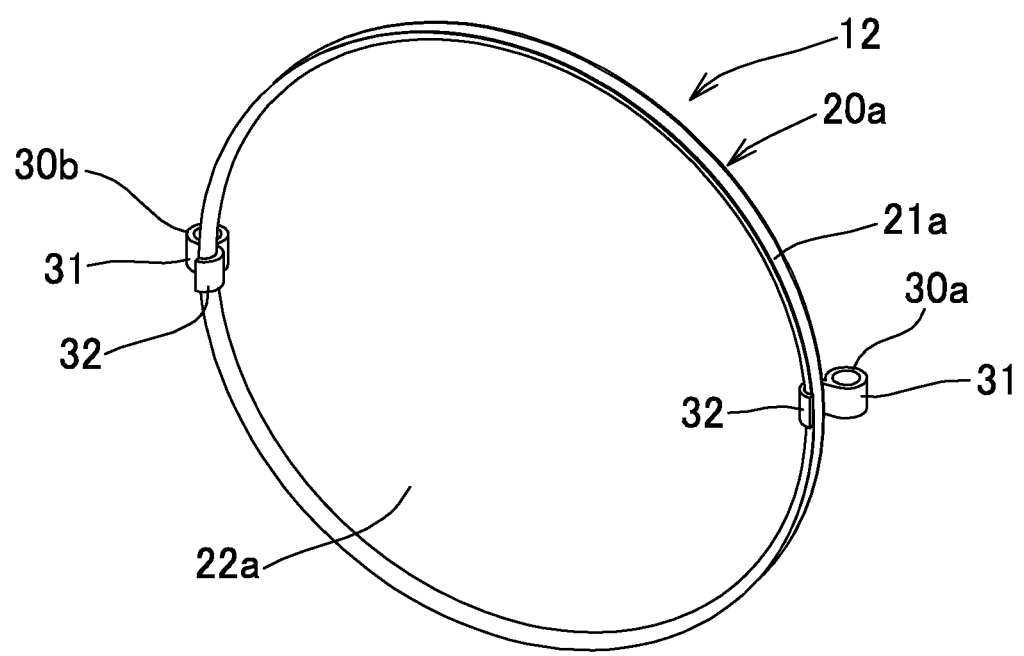
FIG. 5 is a perspective view schematically showing a piece member and parts of connection portions used in the first embodiment of the mold according to one or more embodiments of the present invention.
Figure 6A:
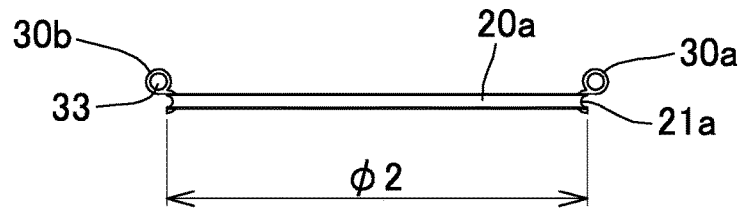
FIG. 6A is a plan view of the piece member and the parts of the connection portions shown in FIG. 5, seen from above of the sheet of FIG. 5.
Figure 6B:
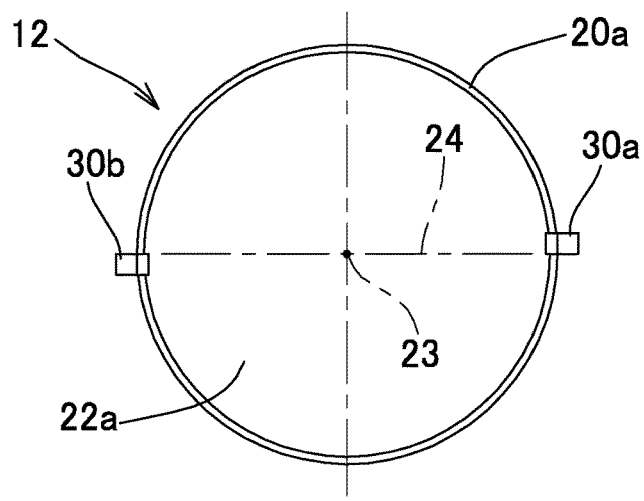
FIG. 6B is a front view of FIG. 6A.
Figure 6C:
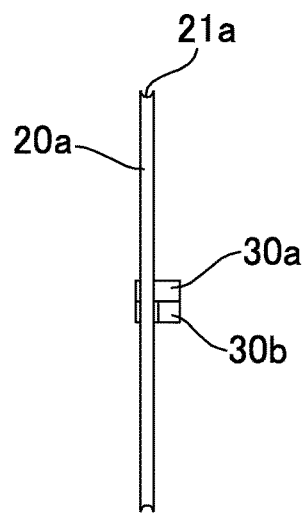
FIG. 6C is a right side view of FIG. 6B.
Figure 7:
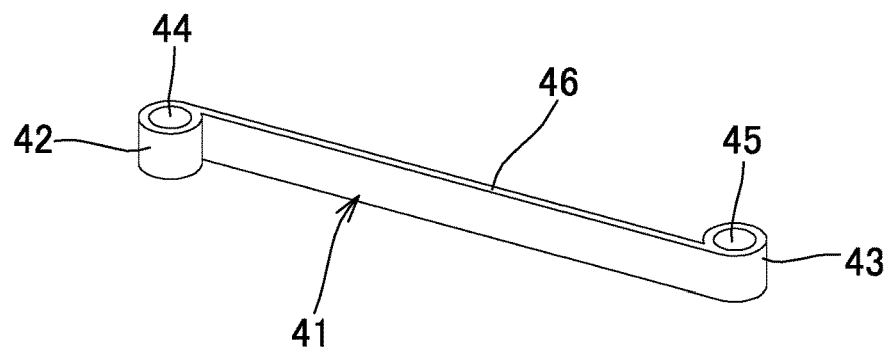
FIG. 7 is a perspective view schematically showing an intermediate shaft portion used in the first embodiment of the mold according to one or more embodiments of the present invention.
Figure 8:
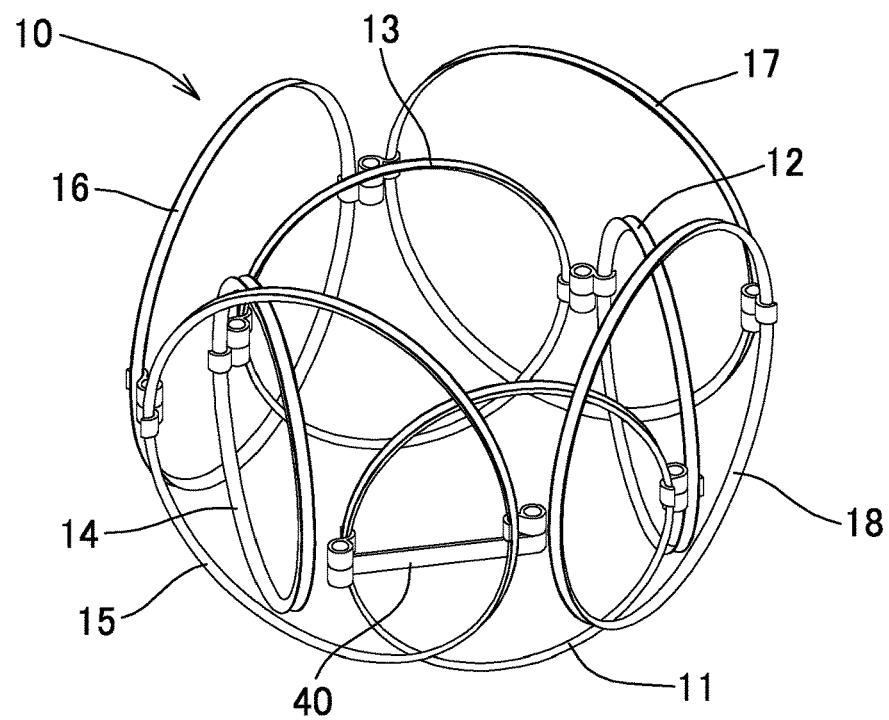
FIG. 8 is a perspective view schematically showing an assembled state of the first embodiment of the mold according to one or more embodiments of the present invention.
Figure 9:
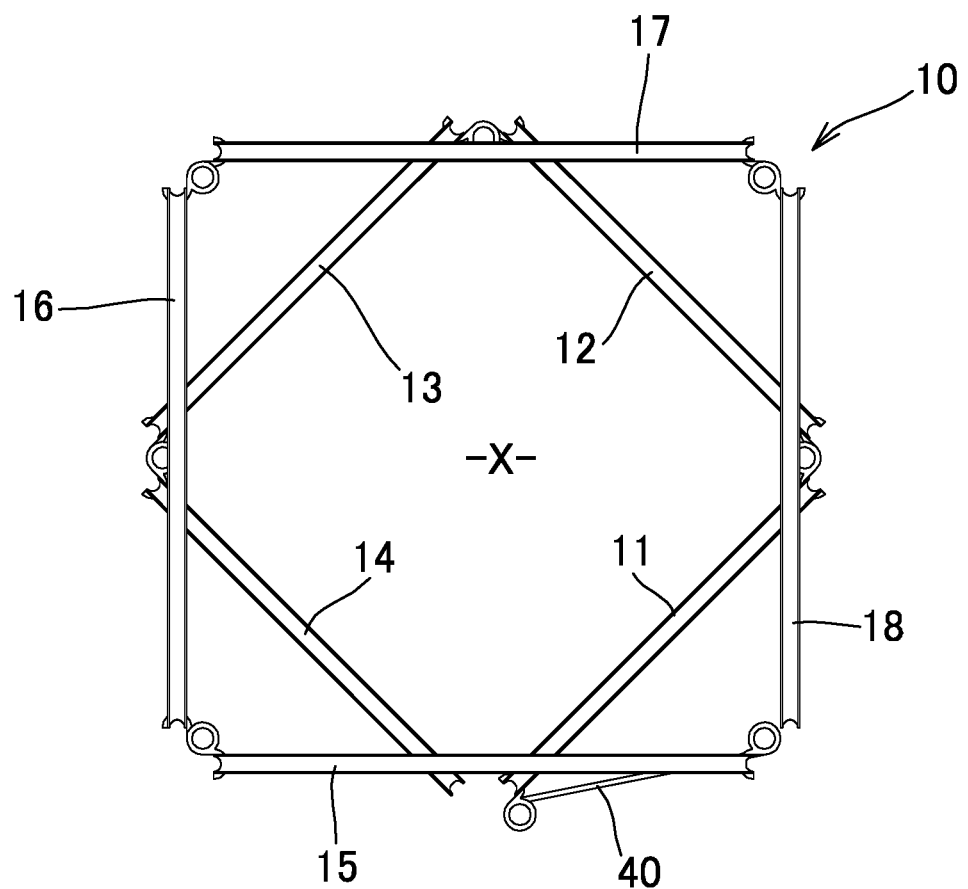
FIG. 9 is a plan view, seen from above of the sheet of FIG. 8.

FIGS. 3 to 9 schematically show a first embodiment of the mold according to the present invention and components thereof. FIG. 3 is a perspective view schematically showing an unfolded state of a mold 10 of the first embodiment. FIG. 4 is a plan view seen from above of the sheet of FIG. 3. FIG. 8 is a perspective view schematically showing an assembled state of the mold 10, and FIG. 9 is a plan view seen from above of the sheet of FIG. 8.

In the mold 10, a transformable member is obtained by connecting a plurality of piece members 11 to 18. In the case where a plurality of piece members are connected to each other to form a transformable member as described above, a mold that can be easily transformed from an assembled state into an unfolded state and from the unfolded state into the assembled state with holding a primary coil can be easily produced as described later. However, in one or more embodiments of the present invention, it is possible to form a transformable member by using a single member that is transformable, without using a plurality of piece members. The piece members 11 to 14 and the piece members 15 to 18 are provided with holding portions 21a and 21 for holding the primary coil.

Figure 28A:
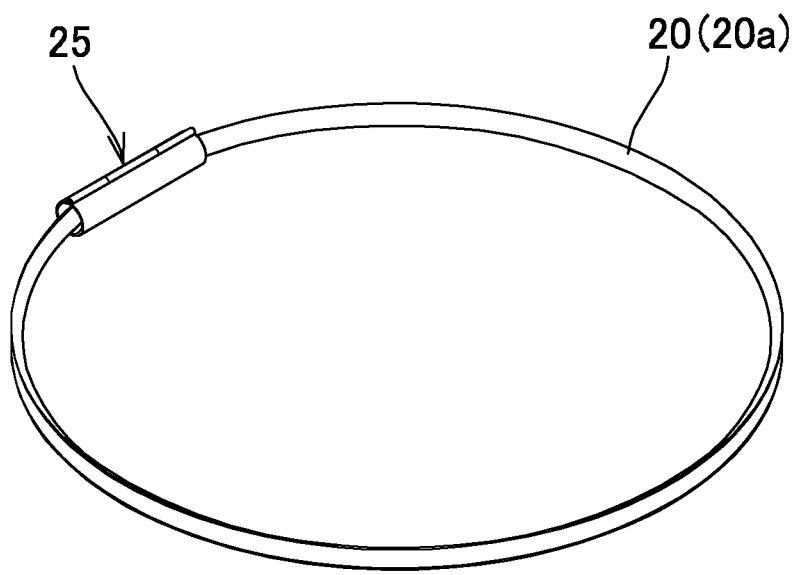
FIG. 28A is a perspective view schematically showing an example of an embodiment of a fixing portion that can be formed at a loop member 20 (20*a*) in the first embodiment of the mold according to one or more embodiments of the present invention.
Figure 28B:
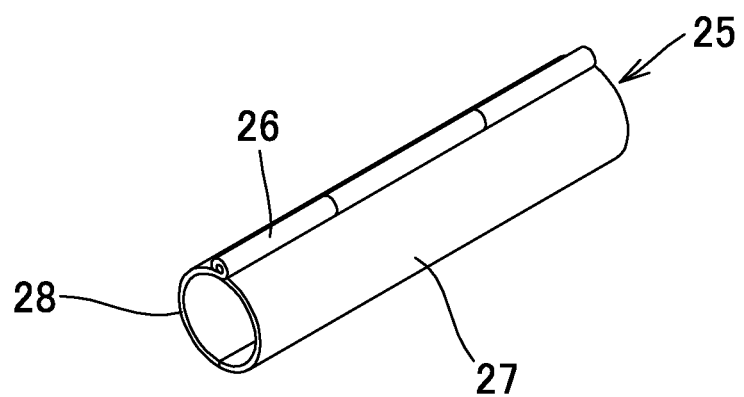
FIG. 28B is an enlarged view of the fixing portion shown in FIG. 28A.

The structure of each of piece members that are usable in one or more embodiments of the present invention is not particularly limited as long as it can have a holding portion for holding the primary coil, and is transformable between an assembled state and an unfolded state so as to allow an outer portion to be arranged at the outer side in the assembled state and an inner portion to be arranged at the inner side of the outer portion, with being connected to the outer portion, in the assembled state. In the present embodiment, as shown in FIG. 3, the piece members 11 to 18 each have a loop structure. Specifically, the piece members 11 to 14 which form an inner portion 19a are each composed of a loop member 20a having a loop structure with a through hole 22a as shown in FIGS. 5, 6A, 6B, 6C, etc. The loop member 20a is provided with the holding portion 21a at the periphery thereof, and the primary coil can be held by the holding portion 21a. The holding portion 21a is formed as a recess over the entire circumference of an outer peripheral side surface portion of the loop member 20a, and the loop member 20a is formed such that the primary coil can be held by the recess. In addition, the recess is open from a center 23 of a circular ring of the loop member 20a toward the outer side in the radial direction, and the primary coil is arranged through this opening onto the recess. Moreover, as shown in FIGS. 4, 6A, 6B, and 6C, the circular ring of each loop member 20a is formed such that the recesses (holding portions 21a) are present on the same plane. The depth of the recess is not particularly limited as long as the primary coil can be held along the recess. For the stable holding of the primary coil, the depth of the recess may be equal to or greater than half the maximum diameter of the primary coil. A fixing portion for preventing the primary coil from falling off of the recess may be provided at the holding portion 21a. Examples of such a fixing portion include (a) a structure provided to cover at least a part, in the circumferential direction, of the opening formed at the recess serving as the holding portion 21a, (b) a structure that narrows the opening in a cross-sectional direction orthogonal to the circumferential direction of the recess, and (c) a structure that extends from an end of the opening in the cross-sectional direction and is narrower than the opening. Examples of the structure of (a) include a hollow tube or annular body that covers a part of the loop member, a tubular body or loop-shaped body made of a member that is reversibly transformable between a linear structure and a helical structure (tubular body) or a loop structure (loop-shaped body), and an arcuate body that is elastically transformable into a linear structure. In addition, the above-described hollow tube or annular body may have a structure that can open/close along the length direction of the primary coil arranged on the recess, or may not have such a structure that can open/close. Examples of the structure that can open/close include a hinge structure. FIG. 28A is a perspective view schematically showing an example of an embodiment of a fixing portion when the fixing portion is provided to the loop member 20 (20a). FIG. 28B is an enlarged view of a fixing portion 25 shown in FIG. 28A. The fixing portion 25 according to the embodiment shown in FIGS. 28A and 28B is a hollow tube (25) that covers a part of the loop member 20 (20a), and the hollow tube (25) has a structure in which two members 27 and 28 each of which has an arcuate cross-sectional shape and which can open/close along the length direction of the primary coil arranged on the recess are connected to each other by a hinge 26. The inner diameter of the hollow tube (25) may be slightly larger than the outer diameter of the primary coil when the primary coil is arranged on the recess. Examples of the structure (c) include an arcuate body that is fixed to the loop member, extends from one end of the opening, and is elastically transformable into a linear structure. The structure (b) or the structure (c) may be provided at a part, in the circumferential direction, of the recess.

In addition, the fixing portion may be provided at one location on a part of the loop member, and may be provided at two locations thereon. Furthermore, the fixing portion may be fixed to the loop member, or may not be fixed to the loop member.

In addition, the piece members 15 to 18 which form an outer portion 19 can also each be composed of a loop member 20 having the same structure as that of the loop member 20a shown in FIGS. 5, 6A, 6B, and 6C. That is, the loop member 20 is configured such that a recess is formed over the entire circumference of an outer peripheral side surface portion thereof and the primary coil can be held by the recess. Moreover, the recess is open from the center of a circular ring of the loop member 20 toward the outer side in the radial direction. In the present embodiment, the structures of the loop members 20 and 20a are different from each other in that the diameter of the loop member 20, which forms the outer portion 19, is larger than that of the loop member 20a, which forms the inner portion 19a. These diameters may be determined as appropriate in accordance with the three-dimensional arrangement of the primary coil. For more stable arrangement of an in-vivo indwelling member (secondary coil) within a bulge, the difference ($\phi 1-\phi 2$) between the diameter ($\phi 1$; see FIG. 4) of the holding portion 21 (recess) of the outer portion 19 and the diameter ($\phi 2$; see FIGS. 4 and 6A) of the holding portion 21a (recess) of the inner portion 19a may be 0.5 mm to 3 mm.

In the present embodiment, the loop members 20a and 20 each have a circular annular shape, but may each have a loop structure with a polygonal shape.

Figure 16:
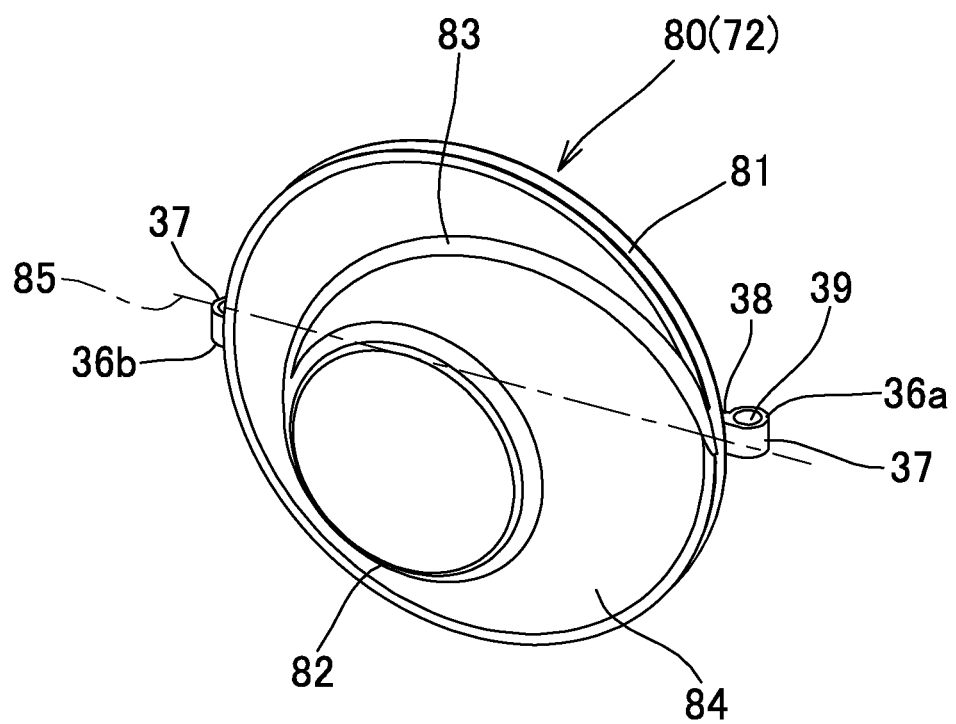
FIG. 16 is a perspective view schematically showing a piece member and parts of connection portions used in the third embodiment of the mold according to one or more embodiments of the present invention.
Figure 17A:
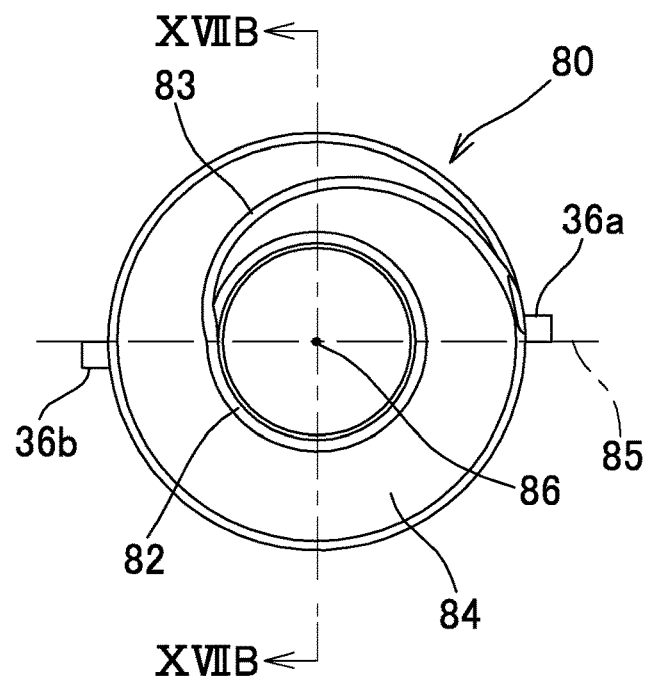
FIG. 17A is a front view of the piece member and the parts of the connection portions shown in FIG. 16.
Figure 17B:
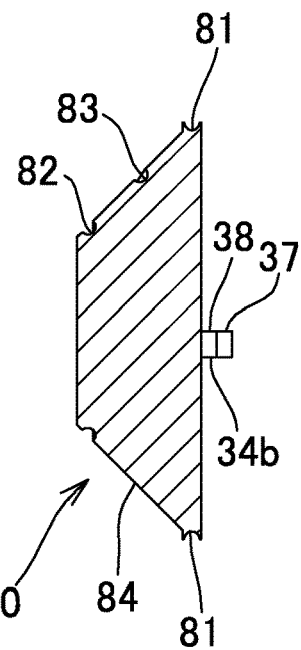
FIG. 17B is a plan view of FIG. 17A.

The piece members 11 to 18 shown in the present embodiment each have a loop structure provided with a through hole. However, in one or more embodiments of the present invention, one of the piece members may have a loop structure. Particularly, since the inner portion should be partially located within the through hole in the assembled state, at least each piece member that forms the outer portion may have a loop structure. When the inner portion can be arranged in this manner in the assembled state, a space formed inside the inner portion (see a portion shown by reference character X in FIG. 9) becomes large, and an in-vivo indwelling member that is the obtained secondary coil can more assuredly ensure a space within a bulge such as a wide-neck aneurysm. In addition, as at least one of the piece members that form the inner portion, for example, a later-described member 80 having a truncated cone shape in which a through hole is not formed and which is shown in FIGS. 16, 17A, and 17B may be used. In such a member 80, helical recesses 82 and 83 are provided as a holding portion on an inclined surface 84, and the member 80 is suitable for the case of forming a helical structure in a part of the three-dimensional arrangement of the primary coil. Such a modification includes, for example, a mold 10a shown in FIG. 23 in which the member 80 shown in FIGS. 16, 17A, and 17B is used instead of the piece member 12 of the mold 10 shown in FIG. 3. As described later, a recess 81 is also formed as a holding portion on an outer peripheral side surface portion, which is the peripheral portion of the member 80, over the entire circumference thereof In addition, in the case of forming a scroll-shaped structure in a part of the three-dimensional arrangement of the primary coil, for example, a plate-shaped member in which a scroll-shaped recess is formed on a flat surface thereof may be used as the piece member instead of the member 80 having a truncated cone shape and an inclined surface, similarly to the member 80.

In the present embodiment, as shown in FIGS. 8 and 9, in the assembled state, the piece members 11 to 14 are arranged at the inner side of the piece members 15 to 18 and form the inner portion 19a. In addition, in the assembled state, the piece members 15 to 18 are arranged at the outer side of the piece members 11 to 14 and form the outer portion 19. Here, the phrase "arranged at the inner side" includes, in addition to the case where all the components of the inner portion are arranged at the inner side of the outer portion, the case where a part of the components of the inner portion is arranged at the inner side of the outer portion. For example, as shown in FIG. 9, in the assembled state of the mold 10, one of the piece members 11 to 14 forming the inner portion 19a and one of connection portions 30 connecting these piece members protrude to the outer side of the piece members 15 to 18 forming the outer portion 19.

In the present embodiment, the piece members 11 to 18, which form the inner portion 19a and the outer portion 19, are connected to each other so as to be linear in the unfolded state as shown in FIGS. 3 and 4. Such linear connection of these piece members in the unfolded state facilitates an operation of holding the primary coil by the mold 10 in the unfolded state. If the piece members 11 to 18 are connected to each other in a straight shape as in the present embodiment, this operation becomes much easier. However, in one or more embodiments of the present invention, for example, as in a third embodiment shown in FIG. 14 described later, piece members 71 to 74 and piece members 75 to 78 which respectively form an inner portion 79a and an outer portion 79, and are a part of a plurality of piece members may be connected in a linear shape, and the inner portion 79a and the outer portion 79 may be connected in a trifurcated shape (see FIG. 15).

At least a part of the piece members is connected in a linear shape, or in a straight shape in the unfolded state, thereby facilitating the operation of holding the primary coil by the mold 10, as described above. Whether to connect a part of the piece members in a linear shape or to connect all the piece members in a linear shape can be determined in accordance with the three-dimensional arrangement of the primary coil. Here, the phrase "linear shape" means that three or more piece members are connected to each other without branching.

In the unfolded state, the piece members 11 to 14 which form the inner portion 19a, and the piece members 15 to 18 which form the outer portion 19, individually have surfaces on which the recesses are formed in the same plane, and the surfaces on which the recesses of all the piece members are located are present on the same plane (see FIG. 4). The recesses of the piece members 11 to 14 and the piece members 15 to 18 are present on the same plane in the unfolded state as described above, thereby facilitating the operation of holding the primary coil by the mold 10. In addition, the recesses of all the piece members are present on the same plane, thereby facilitating this operation much more.

The number of the piece members can be determined in accordance with the three-dimensional structure of the secondary coil. In the present embodiment, the number of the piece members of each of the inner portion 19a and the outer portion 19 is four so that the inner portion 19a and the outer portion 19 each have a square tubular structure in the assembled state. However, for example, the number of the piece members may be any number as long as it is possible to substantially correspond to the shape of the inner wall surface of a bulge such as an aneurysm, and the number of the piece members can be adjusted such that a triangular tubular structure, a pentagonal tubular structure, or a polygonal tubular structure having six or more sides is formed. In addition, the number of the piece members of the inner portion 19a and the number of the piece members of the outer portion 19 may be equal to each other or may be different from each other.

In the present embodiment, as described above, the piece members 11 to 14 form the inner portion 19a, and the piece members 15 to 18 form the outer portion 19. The piece members 11 to 14 and the piece members 15 to 18 are connected such that adjacent piece members are connected to each other by the connection portion 30 which allows the relative positional relationship therebetween to be changed. In addition, the piece member 11 which forms one end portion of the inner portion 19a and the piece member 15 which forms one end portion of the outer portion 19 are connected to each other by a connection portion 40 (hereinafter, also referred to as "intermediate portion") that allows the relative positional relationship between the piece members 11 and 15 to be changed. In the case of such a configuration, the positional relationship between the adjacent piece members can be changed by the connection portion, and it becomes easier to transform the transformable member between the unfolded state and a transformable state while the primary coil is held by the holding portion formed in each piece member. The manner of changing the relative positional relationship between the piece members by the connection portion can be determined as appropriate in accordance with the structure of the secondary coil (the three-dimensional arrangement of the primary coil). In the present embodiment, each connection portion 30 allows the relative positional relationship between the adjacent piece members to be changed so that the piece members 11 to 14 and the piece members 15 to 18 form a straight-shaped structure in the unfolded state and form a loop structure in the assembled state. In addition, the connection portion 40 connects the adjacent piece members 11 and 15 so that: the piece members 11 to 18 form a straight-shaped structure in the unfolded state; and the outer portion 19 is transformed into a loop structure in the assembled state so as to cover the inner portion 19a transformed into an annular structure, from the outside, to form a double loop structure. In the present embodiment, by changing the angle of intersection of the planes on which the recesses (holding portions 21 and 21a) of the loop members 20 and 20a are present between about 0° to 360°, the relative positional relationship between the adjacent piece members is changed.

The structure of each of connection portions that are usable in one or more embodiments of the present invention is not particularly limited as long as it has a function to: connect the adjacent piece members; and transform the transformable member having the plurality of piece members connected to each other between the assembled state and the unfolded state by changing the relative positional relationship between the adjacent piece members. Examples of the structure of each of the connection portions include a hinge, a ring binder, a flexible sheet, and the like, or a combination of these. In addition, in the case where there are a plurality of connection transformable portions, the structures thereof may be the same or different from each other, and, for example, each structure may be at least one type selected from a hinge, a ring binder, and a flexible sheet.

In the present embodiment, as shown in FIGS. 3 to 6, each connection portion 30 is composed of a hinge. Each connection portion 30 includes: a female portion 30a that is provided at a piece member; a female portion 30b that is provided at another piece member adjacent to one side of the piece member; and a male shaft portion that is fitted into through holes 33 provided in the female portions 30a and 30b. The female portions 30a and 30b rotate about the rotation center that is the central axis in the longitudinal direction of the male shaft portion, thereby changing the relative positional relationship between the adjacent piece members. Each of the female portions 30a and 30b has a fitting portion 31 that is provided with the through hole 33 for receiving the male shaft portion for connecting the piece members; and a fixing portion 32 for fixing the female portion 30a or 30b to the piece member. As shown in FIG. 6B, for example, the piece member 12 is composed of the loop member 20a, and the female portion 30a and the female portion 30b are fixed by the fixing portions 32 at the lower side and the upper side of a horizontal axis 24 passing through a central point 23 of the loop member 20a, so as to oppose to each other across the central point 23. The female portions 30a and the female portions 30b are alternately fixed with respect to the horizontal axis 24 as described above, allowing the adjacent piece members to be fixed such that the central points 23 of the respective piece members 11 to 14 are aligned in a straight line. However, in the connection portion between the piece member 11 and the piece member 15, the female portion 30b at the piece member 11 is provided, in the upper side of the horizontal axis 24, at a position corresponding to the female portion 30a. This is different from the position shown in FIG. 6A. In addition, although no female portion 30a is provided at the piece member 14 and no female portion 30b is provided at the piece member 18, a configuration for holding the assembled state of the inner portion and the outer portion may be provided to these piece members.

Each fitting portion 31 is provided so as not to cover the opening side of the holding portion 21 or 21a as shown in FIG. 6A. In addition, the position of each fitting portion 31 with respect to the loop member 20 or 20a is determined in consideration of the direction of rotation of each piece member about the central axis of the male shaft portion as a rotation center. As shown in FIG. 4, the connection portion 30 is provided at each of the piece members 11 to 14 which form the inner portion 19a, such that the fitting portion 31 thereof is located at the upper side of the sheet of FIG. 4, and the connection portion 30 is also provided at each of the piece members 15 to 18, which form the outer portion 19, such that the fitting portion 31 thereof is located at the upper side of the sheet of FIG. 4. That is, in the assembled state, the connection portions 30 are provided such that the fitting portions 31 thereof are located at the side that is the inner side of the inner portion 19a and the outer portion 19.

In the present embodiment, as shown in FIGS. 3, 4, and 7 to 9, the connection portion 40 (intermediate portion) between the inner portion 19a and the outer portion 19 is also composed of a hinge. The connection portion 40 has a structure different from those of the connection portions 30 that connects the piece members forming the inner portion 19a and the piece members forming the outer portion 19, to each other. The connection portion 40 includes (i) female portions 30b and 30a that are fixed to the piece members 11 and 15, (ii) an intermediate shaft portion 41 that connects the inner portion 19a and the outer portion 19 with a predetermined interval provided therebetween, and (iii) two male shaft portions that are fitted into through holes 33, 44, and 45 provided in the female portions 30a and 30b and the intermediate shaft portion 41. The intermediate shaft portion 41 has: a shaft portion 46 that is formed in a straight shape; and female portions 42 and 43 that are provided at both ends of the shaft portion 46, and the through holes 44 and 45 are provided in the female portions 42 and 43, respectively. The female portions 30a and 30b are rotated relative to the intermediate shaft portion 41 about the rotation center that is the central axes in the longitudinal direction of the male shaft portions, thereby changing the relative positional relationship between the piece member 11 and the piece member 15 with the inner portion 19a and the outer portion 19 being connected to each other. Regarding the female portions 30a and 30b that form the connection portion 40, as shown in FIGS. 3 and 4, the female portion 30b is provided at the piece member 11 such that a fitting portion 31 thereof is located at the lower side of the sheets of FIGS. 3 and 4, and the female portion 30a is provided at the piece member 15 such that a fitting portion 31 thereof is located at the upper side of the sheets of FIGS. 3 and 4. That is, the female portion 30b is provided at the piece member 11 which forms the inner portion 19a, such that the fitting portion 31 thereof is located at the outer side of the inner portion 19a in the assembled state, and the female portion 30a is provided at the piece member 15 which forms the outer portion 19, such that the fitting portion 31 thereof is located at the inner side of the outer portion 19 in the assembled state.

Figure 11:
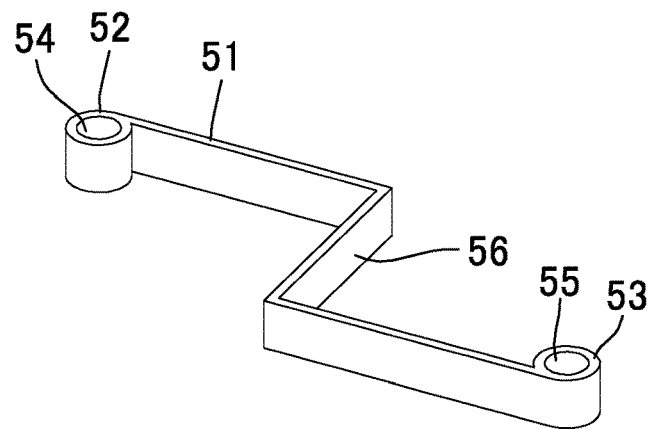
FIG. 11 is a perspective view schematically showing an intermediate shaft portion used in the second embodiment of the mold according to one or more embodiments of the present invention.

For the structure of the intermediate shaft portion 41, it is merely required that the inner portion can be arranged at the inner side of the outer portion, while the inner portion and the outer portion are connected to each other, upon transforming the transformable member from the unfolded state into the assembled state. The structure can be determined as appropriate in consideration of the manner of transforming the transformable member into the assembled state and the structure of the transformable member in the assembled state. In the present embodiment, the intermediate shaft portion 41 has the shaft portion 46 having a straight and elongated plate shape, and the female portions 42 and 45 are provided at both end portions of the shaft portion 46. The female portions 42 and 43 are provided so as to face the individual sides different from each other with the axis in the longitudinal direction of the shaft portion 46 as a center line, and the axial directions of the through holes 44 and 45 are parallel to the crosswise direction of the shaft portion 46. However, as shown in FIG. 11 described later, the shaft portion may not have a straight shape and may have a crank-shaped structure, or and the female portions 42 and 45 may be provided so as to face the same side of the shaft portion 46.

The materials forming the piece members and the connection portions are not particularly limited, and examples of the materials include metals, resins, ceramic, and glass. However, the materials may have heat resistance, since heat treatment is performed on a mold on which the primary coil is arranged and which is in the assembled state, as described later. The heat resistant temperature is different depending on the conditions of the heat treatment, and may not be lower than 700° C., such as not lower than 1000° C.

A method for fixing the piece member and the female portion which forms the connection portion, may be selected as appropriate in accordance with a material to be used or other factors. For example, adhesion, deposition, welding, caulking, screwing, and the like can be adopted for the method.

The materials forming the piece members and the connection portions, and the method for fixing the piece member and the female portion forming the connection portion can be applied to other embodiments described later.

Hereinafter, the case of transforming the mold 10 from the unfolded state into the assembled state will be described.

In the mold 10 in the unfolded state shown in FIGS. 3 and 4, the piece members 12 to 14 to which the female portions 30b are fixed are moved in the direction of an arrow (counterclockwise) in FIG. 4 about the individual rotation centers that are the respective female portions 30b in the inner portion 19a, thereby transforming the inner portion 19a that is in a straight shape in the unfolded state into a square tubular shape. Accordingly, the inner portion 19a is made into the assembled state. In addition, the intermediate shaft portion 41 is moved in the direction of an arrow (counterclockwise) about the female portion 30b (female portion 43) of the intermediate portion 40, and the piece members 15 to 18 to which the female portions 30a are fixed are also moved in the direction of an arrow (counterclockwise) in FIG. 4 about the individual rotation centers that are the respective female portions 30a in the outer portion 19, thereby transforming the outer portion 19 that is in a straight shape in the unfolded state into a square tubular shape. Accordingly, the outer portion 19 is made into the assembled state. At this time, as shown in FIG. 9, the side of the piece member 11 at which the female portion 30b is fixed and the side of the piece member 14 at which the female portion 30a is not fixed are partially located within a through hole 22 of the piece member 15, the side of the piece member 13 at which the female portion 30a is fixed and the side of the piece member 14 at which the female portion 30b is fixed are partially located within the through hole 22 of the piece member 16, the side of the piece member 12 at which the female portion 30a is fixed and the side of the piece member 13 at which the female portion 30b is fixed are partially located within the through hole 22 of the piece member 17, and the side of the piece member 11 at which the female portion 30a is fixed and the side of the piece member 12 at which the female portion 30b is fixed are partially located within the through hole 22 of the piece member 18. More specifically, in the present embodiment, the mold 10 is configured such that the respective piece members 11 to 14 which form the inner portion 19a, and the connection portions 30 and 40 partially project from the through holes 22 of the respective piece members 15 to 18 which form the outer portion 19, in the assembled state.

Next, a second embodiment of the mold according to the present invention will be described.

Figure 10:
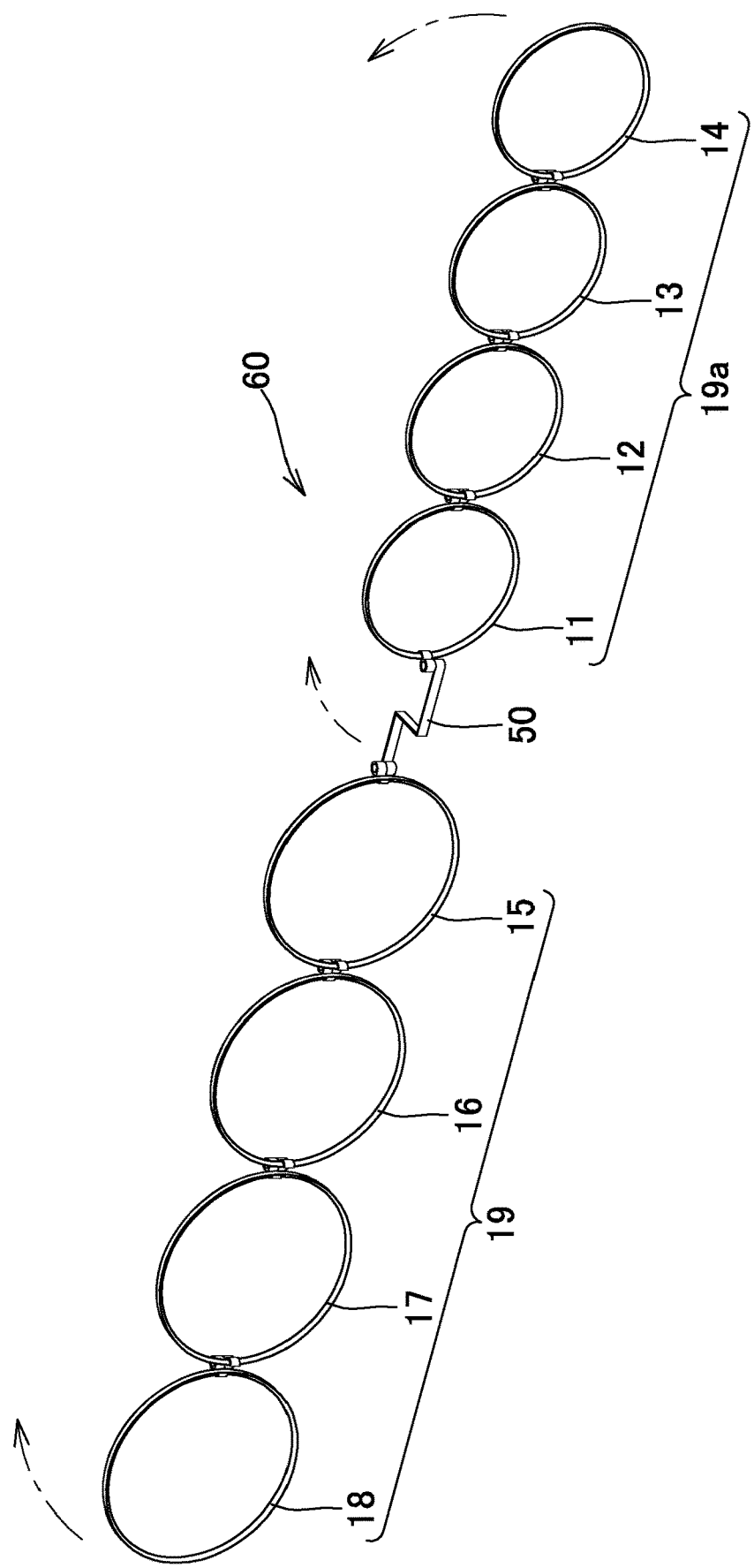
FIG. 10 is a perspective view schematically showing an unfolded state of a second embodiment of the mold according to one or more embodiments of the present invention.
Figure 12:
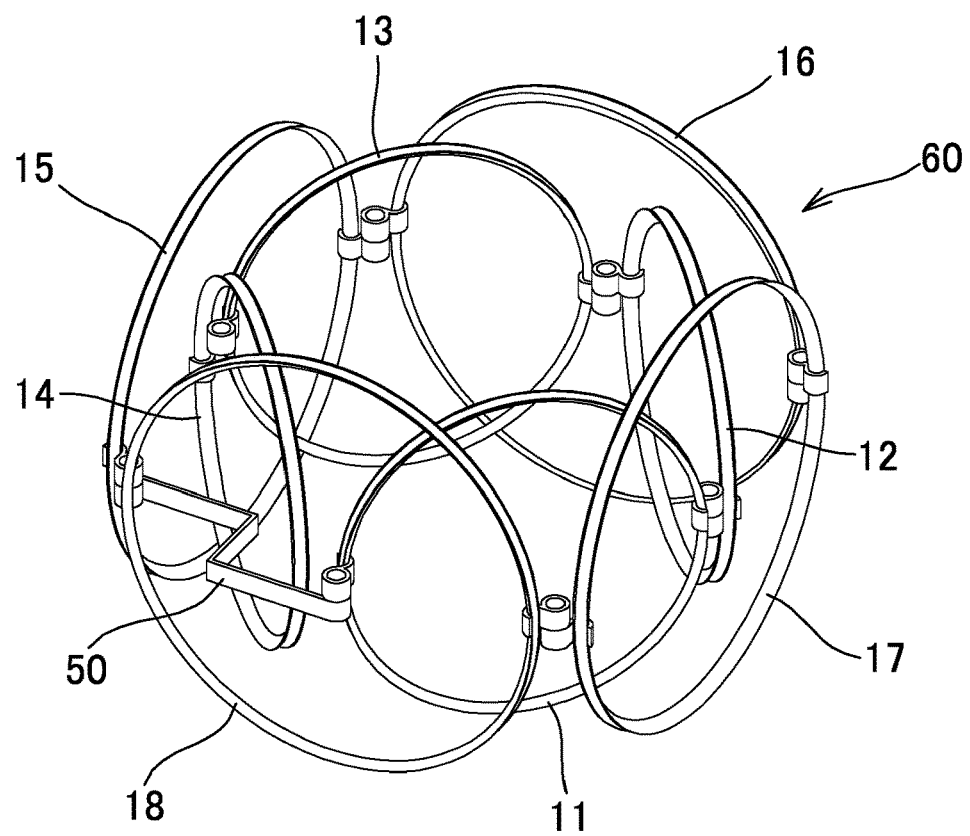
FIG. 12 is a perspective view schematically showing an assembled state of the second embodiment of the mold according to one or more embodiments of the present invention.
Figure 13:
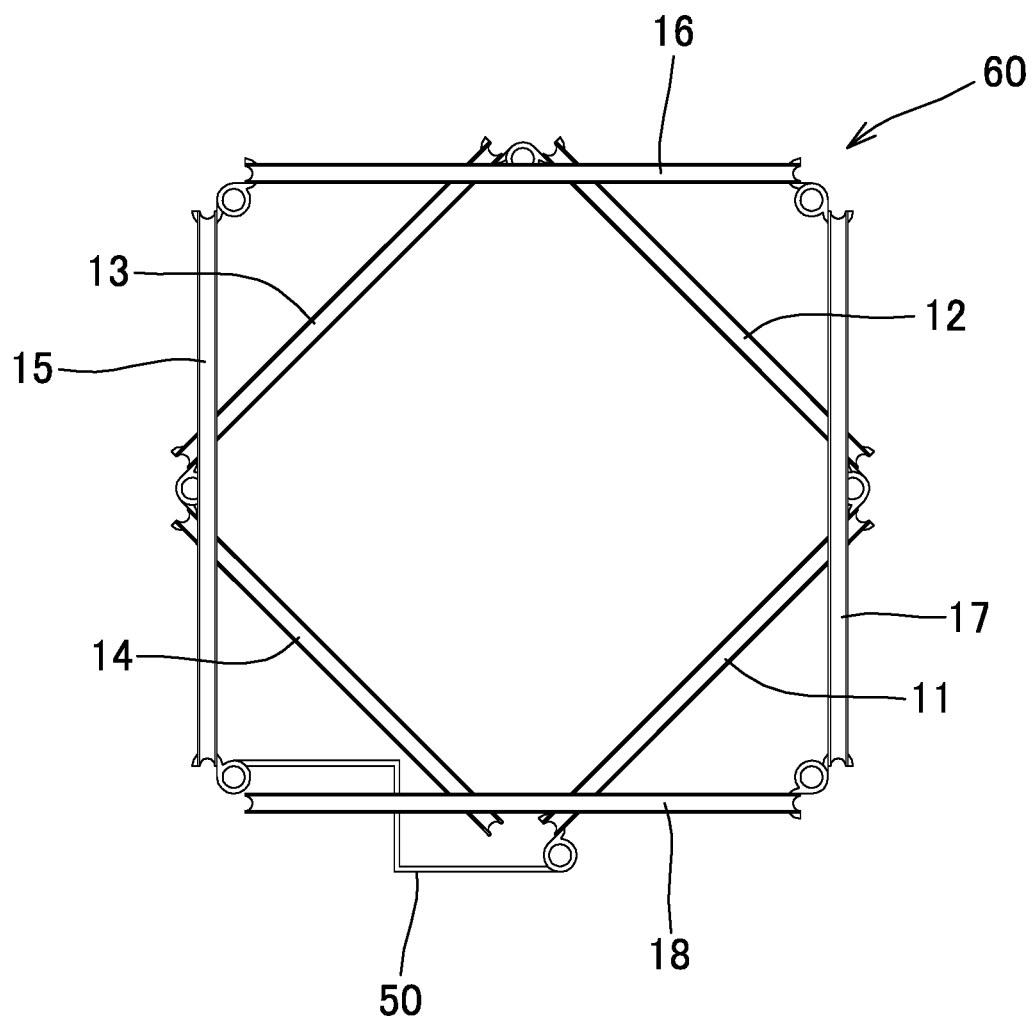
FIG. 13 is a plan view of the mold shown in FIG. 12, seen from above of the sheet of FIG. 12.

FIGS. 10 to 13 schematically show the second embodiment of the mold according to the present invention and components thereof. FIG. 10 is a perspective view schematically showing an unfolded state of a mold 60 of the second embodiment. FIG. 12 is a perspective view schematically showing an assembled state of the mold 60, and FIG. 13 is a plan view seen from above of the sheet of FIG. 12.

The mold 60 of the present embodiment has the same configuration as in the first embodiment, except that the intermediate shaft portion 41 in the mold 10 of the first embodiment is changed to an intermediate shaft portion 51 shown in FIG. 11 and the arrangement of the outer portion 19 with respect to the inner portion 19a in the assembled state is different. Therefore, the same components are designated by the same reference characters, and the different components will be described below.

The intermediate shaft portion 51 used in the mold 60 of the present embodiment has: an elongated shaft portion 56 having a portion formed in a crank shape; and female portions 52 and 53 provided at both ends of the shaft portion 56, and through holes 54 and 55 are provided in the female portions 52 and 53, respectively. The female portions 30a and 30b are rotated relative to the intermediate shaft portion 51 about the individual rotation centers that are the respective central axes in the longitudinal direction of the male shaft portions, thereby changing the relative positional relationship between the piece member 11 and the piece member 15, while the inner portion 19a and the outer portion 19 are connected to each other.

As shown in FIG. 11, the shaft portion 56 has: two parallel elongated plate-shaped portions (long shaft portions) extending in a straight shape; and a plate-shaped portion (short shaft portion) continuing orthogonally to these parallelly elongated plate-shaped portions so as to connect them. The shaft portion 56 is formed in a crank shape by the short shaft portion and both long shaft portions in the vicinity of the short shaft portion. The shaft portion 56 is formed in a crank shape as described above, so that the outer portion 19 and the inner portion 19a can be transformed into a desired assembled structure upon transformation of the outer portion 19 and the inner portion 19a into the assembled state, while the outer portion 19 and the inner portion 19a are connected to each other (see FIG. 13). Therefore, the shape of the shaft portion 56 is not limited to the crank shape as long as such a function can be exerted, and can be changed as appropriate in accordance with the structure of each piece member, the manner of transforming the transformable member, and the like. Examples of the shape of the shaft portion 56 include a shape in which the angle of intersection of the short shaft portion and each long shaft portion is made gentle, and a shape formed by a gentle curve such as an S shape.

As shown in FIG. 11, the female portions 52 and 53 face the mutually different sides with the axes in the longitudinal direction of the long shaft portions of the shaft portion 56 as center lines, and the axial directions of the through holes 54 and 55 respectively provided in the female portions 52 and 53 are parallel to the crosswise direction of the short shaft portion of the shaft portion 56.

Hereinafter, the case of transforming the mold 60 from the unfolded state into the assembled state will be described.

In the present embodiment, the rotation direction of an intermediate portion 50 is different from that in the first embodiment, but the others are the same as in the first embodiment. Specifically, the piece members 12 to 14 to which the female portions 30b are fixed are moved in the direction of an arrow (counterclockwise) in FIG. 10 about the individual rotation centers that are the respective female portions 30b in the inner portion 19a, thereby transforming the inner portion 19a that is in a straight shape in the unfolded state into a square tubular shape. Accordingly, the inner portion 19a is made into the assembled state. In addition, the intermediate shaft portion 51 is moved in the direction of an arrow (clockwise) about the female portion 30b (female portion 53) of the intermediate portion 50, and the piece members 15 to 18 to which the female portions 30a are individually fixed are also moved in the direction of an arrow (counterclockwise) in FIG. 10 about the individual rotation centers that are the respective female portions 30a in the outer portion 19, thereby transforming the outer portion 19 that is in a straight shape in the unfolded state into a square tubular shape. Accordingly, the outer portion 19 is made into the assembled state. At this time, as shown in FIG. 13, the side of the piece member 14 at which the female portion 30b is fixed and the side of the piece member 13 at which the female portion 30a is fixed are partially located within the through hole 22 of the piece member 15, the side of the piece member 12 at which the female portion 30a is fixed and the side of the piece member 13 at which the female portion 30b is fixed are partially located within the through hole 22 of the piece member 16, the side of the piece member 11 at which the female portion 30a is fixed and the side of the piece member 12 at which the female portion 30b is fixed are partially located within the through hole 22 of the piece member 17, and the side of the piece member 11 at which the female portion 30a is fixed and the side of the piece member 14 at which the female portion 30b is not fixed are partially located within the through hole 22 of the piece member 18. More specifically, in the present embodiment, the mold 60 is configured such that the respective piece members 11 to 14 which form the inner portion 19a, and the connection portions 30 and 50 partially project from the through holes 22 of the respective piece members 15 to 18 which form the outer portion 19, in the assembled state.

Next, a third embodiment of the mold according to the present invention will be described.

Figure 14:
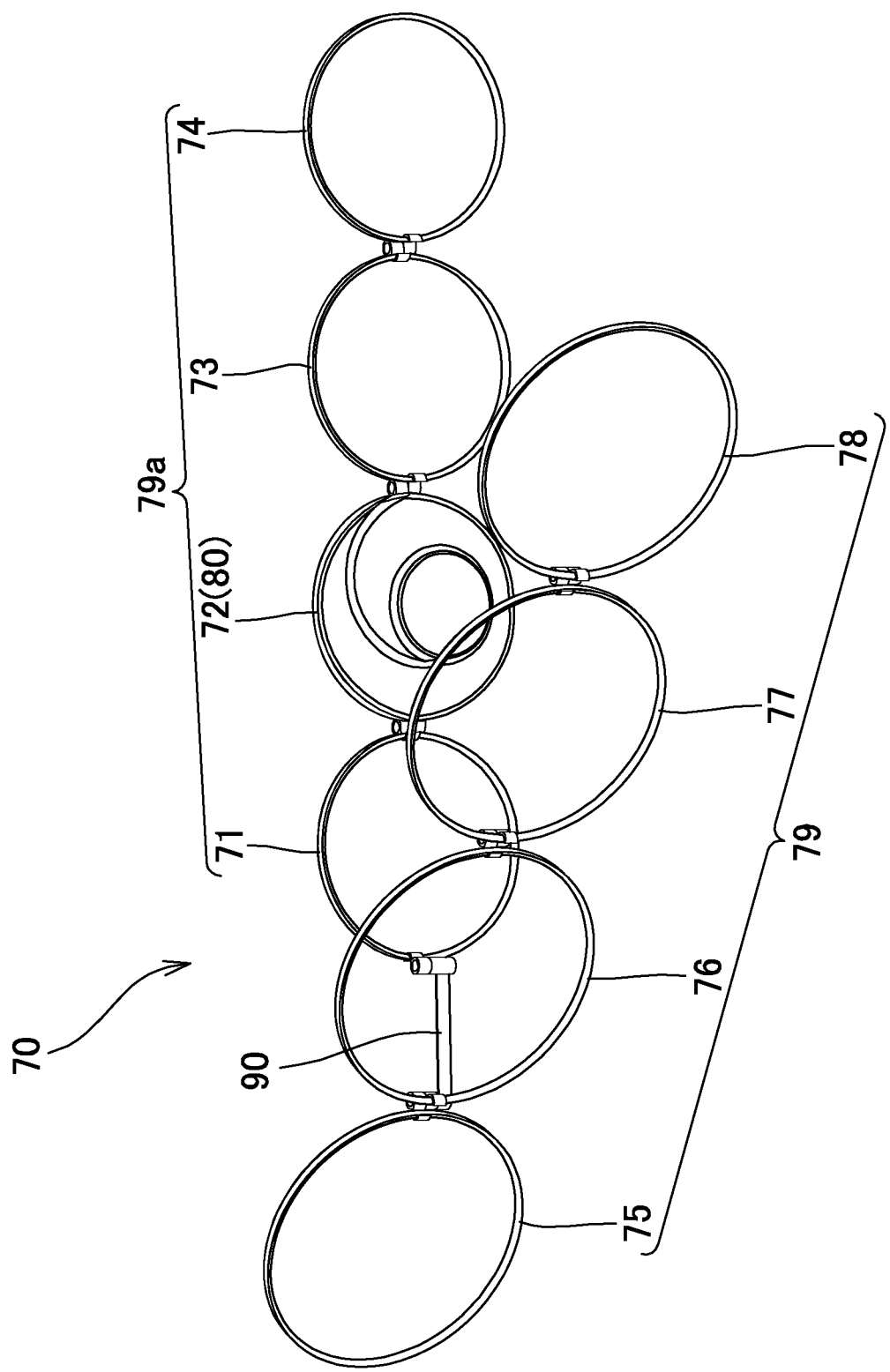
FIG. 14 is a perspective view schematically showing an unfolded state of a third embodiment of the mold according to one or more embodiments of the present invention.
Figure 15:
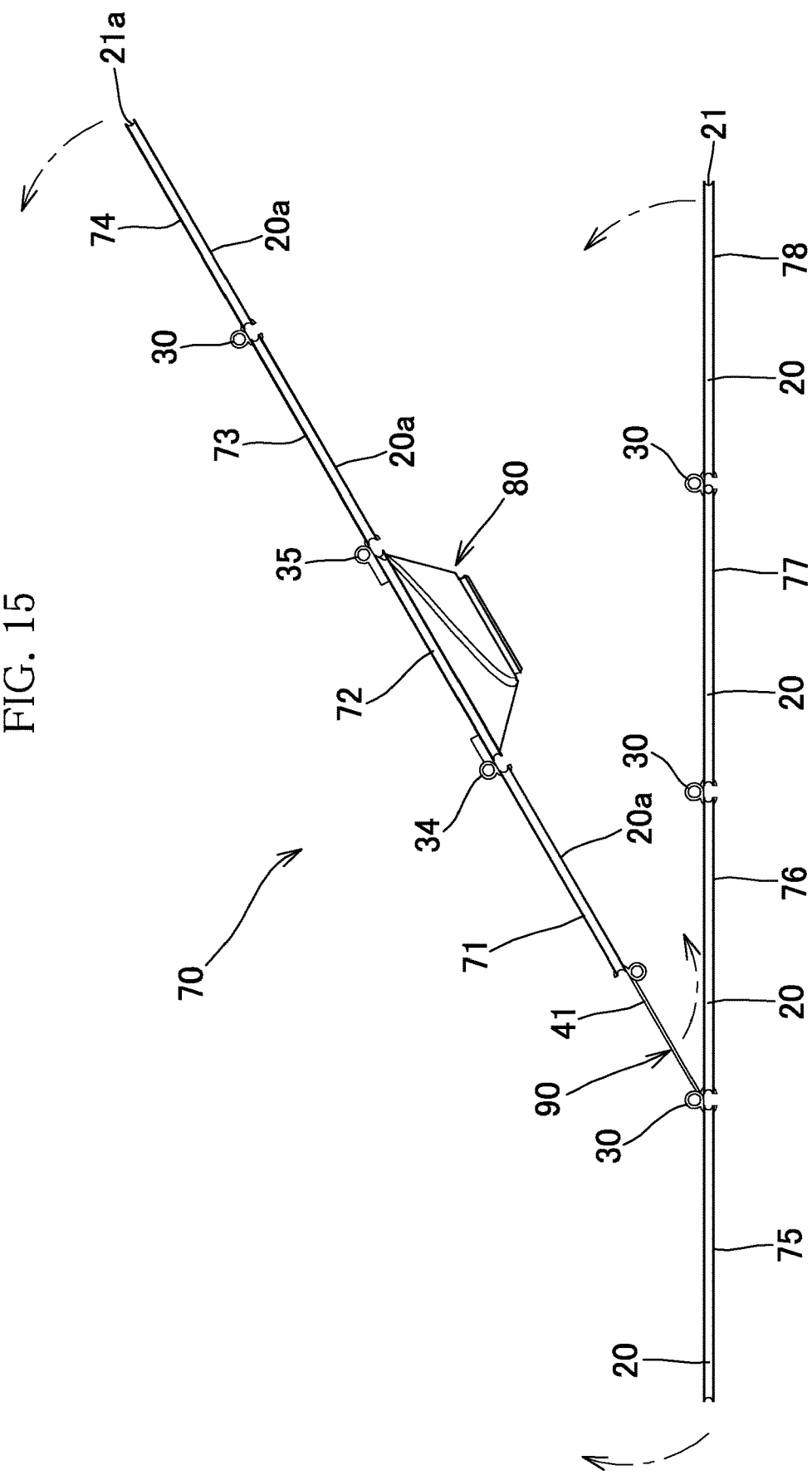
FIG. 15 is a plan view of the mold shown in FIG. 14, seen from above of the sheet of FIG. 14.
Figure 18:
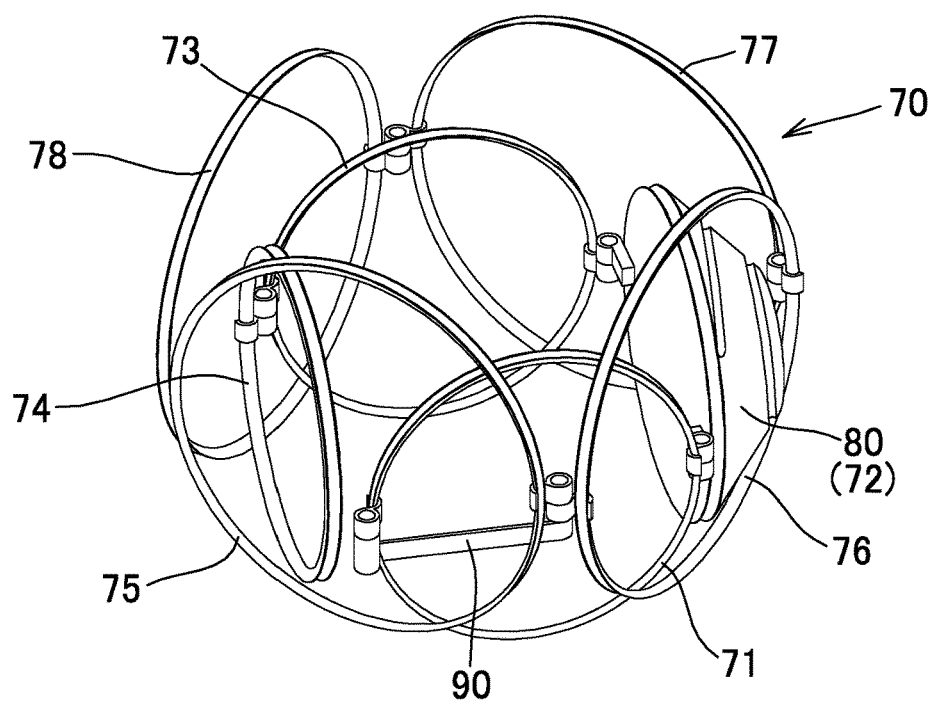
FIG. 18 is a perspective view schematically showing an assembled state of the third embodiment of the mold according to one or more embodiments of the present invention.
Figure 19:
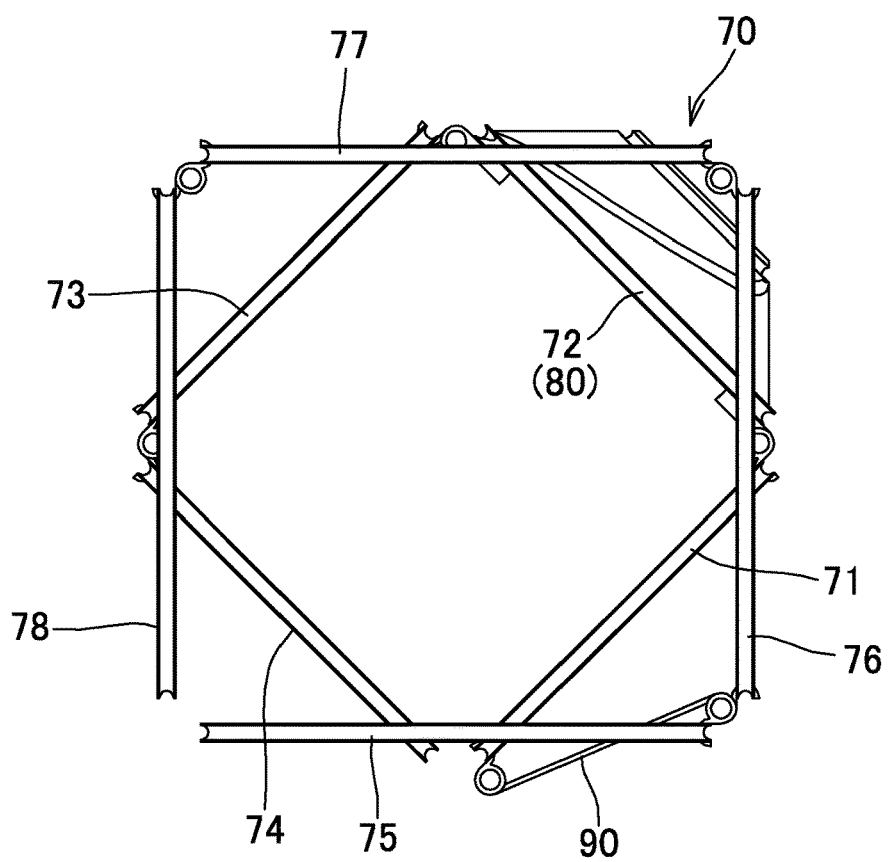
FIG. 19 is a plan view of the mold shown in FIG. 18, seen from above of the sheet of FIG. 18.

FIGS. 14 to 19 schematically show the third embodiment of the mold according to the present invention and components thereof. FIG. 14 is a perspective view schematically showing an unfolded state of a mold 70 of the third embodiment, and FIG. 15 is a plan view seen from above of the sheet of FIG. 14. FIG. 18 is a perspective view schematically showing an assembled state of the mold 70, and FIG. 19 is a plan view seen from above of the sheet of FIG. 18.

The mold 70 according to the present embodiment includes a transformable member that includes: the inner portion 79a including the piece members 71 to 74; and the outer portion 79 including the piece members 75 to 78. The piece members 71 to 74 are connected to each other by connection portions 30, 34, and 35 so as to be straight in the unfolded state, and the piece members 75 to 78 are connected to each other by connection portions 30 so as to be straight in the unfolded state. In addition, the inner portion 79a and the outer portion 79 are connected to each other by an intermediate portion (connection portion) 90 so as to be straight in the unfolded state.

Similarly to the case of the first embodiment, the piece members 71, 73, and 74 are each composed of a loop member 20a having a loop structure, and the piece member 72 is composed of the member 80 in which no through hole is formed as shown in FIGS. 16, 17A, and 17B. In the present embodiment, the member 80 has a truncated cone shape. The recesses 82 and 83 which are formed in a helical shape are provided, as a holding portion, on the inclined surface 84 of the member 80. The recesses having such a structure allows a helical structure to be formed in a part of the three-dimensional arrangement of the primary coil. In addition, the recess 81 is also formed as a holding portion on the outer peripheral surface, which is the peripheral portion of the member 80, over the entire circumference thereof, and the primary coil can be held along at least a part of the recess 81. The recess 81 is open from a center 86 of the member 80 toward the outer side in the radial direction, and the primary coil is arranged through this opening onto the recess. Each of the depths of the recesses 81 to 83 is not particularly limited as long as the primary coil can be held along the recess. For stable holding of the primary coil, each of the depths of the recesses 81 to 83 may be equal to or greater than half of the maximum diameter of the primary coil. In the present embodiment, the member 80 has a truncated cone shape, but a scroll-shaped structure can be provided on a flat surface of a plate-shaped plane member, and a scroll-shaped structure can be formed in a part of the three-dimensional arrangement of the primary coil. A fixing portion for preventing the primary coil from falling off of the recess may be provided at each of the recesses 81, 82, and 83 of the member 80. Examples of such a fixing portion include a structure that covers at least a part of the opening formed at the recess 81, 82, or 83.

Similarly to the case of the first embodiment, the piece members 75 to 78 are each composed of a loop member 20 having a loop structure.

Similarly to the first embodiment, the piece member 73 and the piece member 74 are connected to each other by the connection portion 30. The piece members 71 and 72 are connected to each other by the connection portion 34, and the piece members 72 and 73 are connected to each other by the connection portion 35. Each of the connection portions 34 and 35 is composed of a hinge, and the function thereof is the same as that of each connection portion 30 in the first embodiment. Similarly to the piece member 11, the connection portion 34 includes: a female portion 30a that is fixed to the piece member 71; a female portion 36b that is fixed to the piece member 72; and a male shaft portion that is fitted into a through hole 33 formed in the female portion 30a and a through hole 39 formed in the female portion 36b. The connection portion 35 includes: a female portion 30b that is fixed to the piece member 73 similarly to the piece member 13; a female portion 36a that is fixed to the piece member 72; and a male shaft portion that is fitted into a through hole 33 formed in the female portion 30b and a through hole 39 formed in the female portion 36a. The female portions 30a, 30b, 36a, and 36b rotate about the individual rotation centers that are the respective central axes in the longitudinal direction of the male shaft portions, thereby changing the relative positional relationship between the adjacent piece members.

The female portion 36a and the female portion 36b have the same structure, and each have: a fitting portion 37 that is provided with the through hole 39 for receiving the male shaft portion for connecting the piece members; and a fixing portion 38 for fixing the female portion 30a or 30b to the piece member 72. Similarly to the case of the loop members 20 and 20a of the first embodiment, regarding the fixed positions of the female portions 36a and 36b to the member 80, they are fixed by, for example, the fixing portions 38 at the upper side and the lower side of a horizontal axis 85 passing through the central point 86 of the member 80, so as to oppose each other across the central point 86 as shown in FIG. 17A. The fitting portion 37 is provided so as not to cover the opening side of the recess 81 (see FIG. 15). In addition, the position of the fitting portion 37 with respect to the loop member 20a is determined in consideration of the direction in which the piece member is rotated about the central axis of the male shaft portion.

In the present embodiment, as shown in FIG. 15, the piece member 71 that serves as the one end of the piece members that form the inner portion 79a is connected between the piece member 75 and the piece member 76 of the outer portion 79 via the intermediate portion 90, and the inner portion 79a and the outer portion 79 are connected to each other in a trifurcated shape. More specifically, the piece members that form each of the inner portion 79a and the outer portion 79 are linearly connected with each other so that the recesses thereof are present on the same plane in the unfolded state. The inner portion 79a and the outer portion 79 are connected with each other so that, in the unfolded state, crosswise directions orthogonal to the longitudinal directions of the respective portions 79a and 79 are parallel to each other and the planes on which the respective portions are present intersect each other. The function of the intermediate portion 90 is the same as that of the intermediate portion 40 in the first embodiment. The intermediate portion 90 includes (i) an intermediate shaft portion 41 that connects the inner portion 79a and the outer portion 79 with a predetermined interval provided therebetween, (ii) a female portion 30b that is fixed to the piece member 71, (iii) a female portion 30a that is fixed to the piece member 75, (iv) a female portion 30b that is fixed to the piece member 76, and (v) two male shaft portions that are fitted into through holes 33, 44, and 45 provided in the female portions 30a and 30b and the intermediate shaft portion 41. The connection portion 30 that connects the piece member 75 and the piece member 76 is formed by (iv) the female portion 30b that is fixed to the piece member 76, (iii) the female portion 30a that is fixed to the piece member 75, and (v) the male shaft portion that is fitted into the through holes 33 provided in the female portions 30a and 30b.

In the intermediate portion 90, in a state where the intermediate shaft portion 41 shown in FIG. 7 is inverted upside down, the female portion 30b that is fixed to the piece member 71 and the female portion 43 of the intermediate shaft portion 41 are connected to each other via the male shaft portion, and the female portion 30a that is fixed to the piece member 75, the female portion 30b that is fixed to the piece member 76, and the female portion 42 of the intermediate shaft portion 41 are connected to each other via the male shaft portion.

Hereinafter, the case of transforming the mold 70 from the unfolded state into the assembled state will be described.

First, the piece members 72 to 74 to which the female portions 30b and 36b are fixed are moved in the direction of an arrow (counterclockwise) in FIG. 15 about the individual rotation centers that are the respective female portions 30b and 36b in the inner portion 79a, thereby transforming the inner portion 79a that is in a straight shape in the unfolded state into a square tubular shape. Accordingly, the inner portion 79a is made into the assembled state. In addition, the intermediate shaft portion 41 is moved in the direction of an arrow (counterclockwise) in FIG. 15 about the female portion 30b (female portion 42) of the intermediate portion 90, the piece member 75 is also moved in the direction of an arrow (clockwise) in FIG. 15 about the female portion 30a at the piece member 75 of the outer portion 19, and the piece members 76 to 78 are moved in the direction of an arrow (counterclockwise) in FIG. 15 about the individual rotation centers that are the respective female portions 30a at the piece members 76 to 78 of the outer portion 79. With the above, the outer portion 79 that is in a straight shape in the unfolded state is transformed into a square tubular shape, so as to be made into the assembled state. At this time, as shown in FIG. 19, the side of the piece member 74 at which the female portion 30b is not fixed and the side of the piece member 71 at which the female portion 30b is fixed are partially located within the through hole 22 of the piece member 15, the side of the piece member 71 at which the female portion 30a is fixed and the side of the piece member 72 at which the female portion 30b is fixed are partially located within the through hole 22 of the piece member 76, the side of the piece member 72 at which the female portion 36a is fixed and the side of the piece member 73 at which the female portion 36b is fixed are partially located within the through hole 22 of the piece member 77, and the side of the piece member 73 at which the female portion 30a is fixed and the side of the piece member 74 at which the female portion 30b is fixed are partially located within the through hole 22 of the piece member 78. More specifically, in the present embodiment, the mold 70 is configured such that the respective piece members 71 to 74 which form the inner portion 79a, and the connection portions 30, 34, 35, and 90 partially project from the through holes 22 of the respective piece members 75 to 78 which form the outer portion 79, in the assembled state.

Next, a fourth embodiment of the mold according to the present invention will be described.

Figure 20:
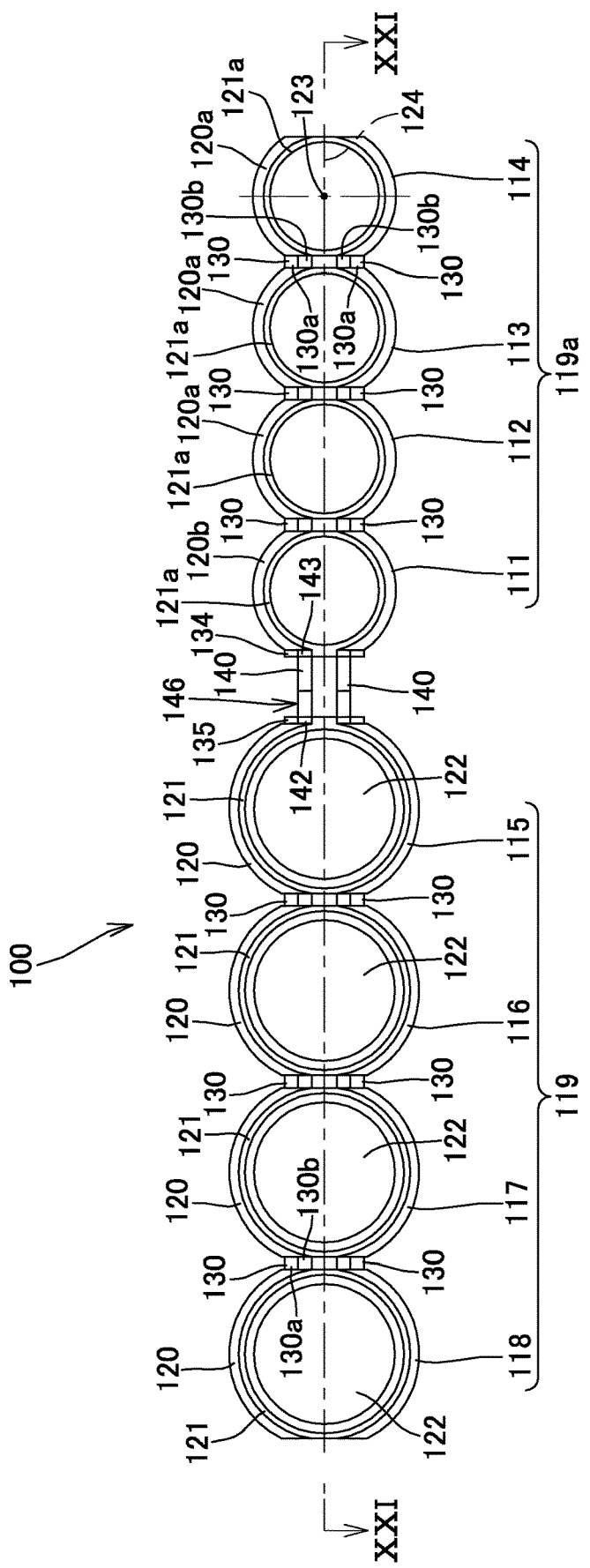
FIG. 20 is a perspective view schematically showing an unfolded state of a fourth embodiment of the mold according to one or more embodiments of the present invention.
Figure 21:
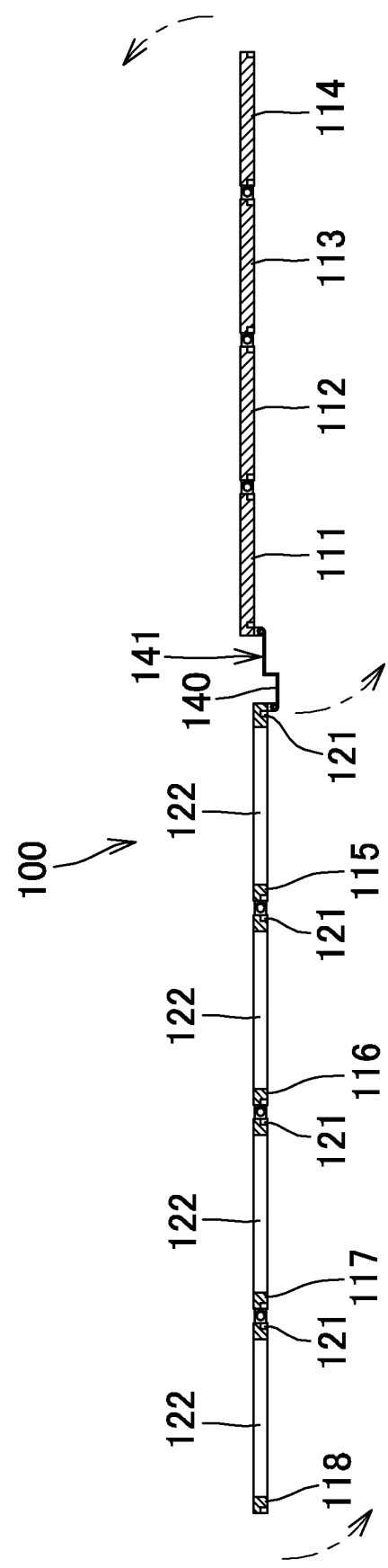
FIG. 21 is a cross-sectional view of FIG. 20, taken along the line II-II.
Figure 22:
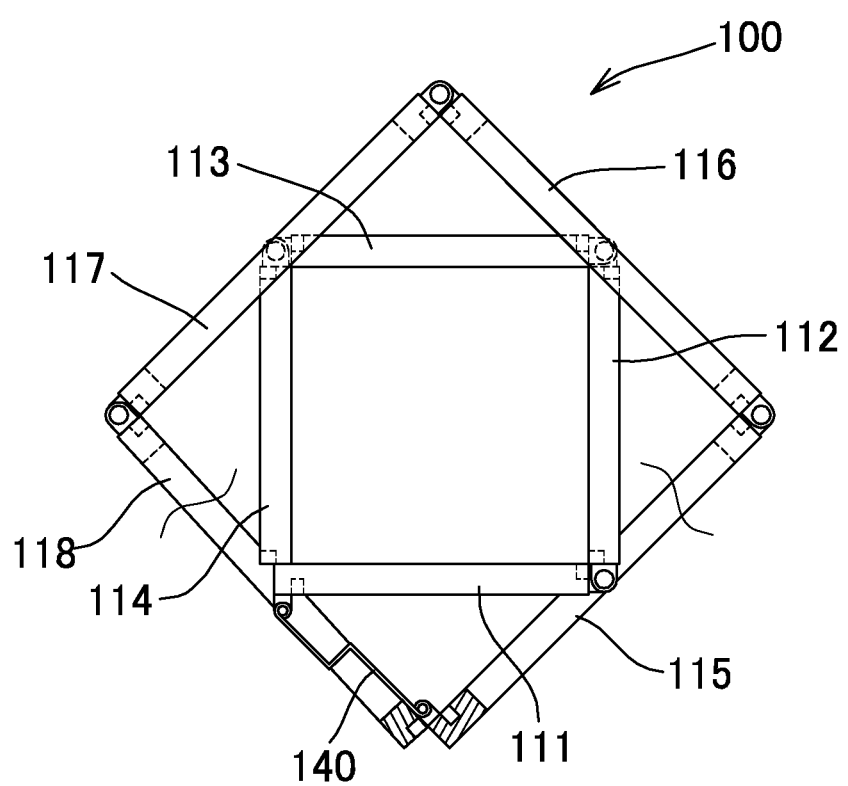
FIG. 22 is a partially cutaway plan view schematically showing an assembled state of the fourth embodiment of the mold according to one or more embodiments of the present invention.

FIGS. 20 to 22 schematically show the fourth embodiment of the mold according to the present invention. FIG. 20 is a front view schematically showing an unfolded state of a mold 100 of the fourth embodiment. FIG. 21 is a cross-sectional view taken along the line II-II in FIG. 20. FIG. 22 is a partially cutaway plan view schematically showing an assembled state of the mold 100 seen from above of the sheet of FIG. 20.

The mold 100 includes a transformable member that includes: an inner portion 119a; an outer portion 119; and an intermediate portion (connection portion) 140 that connects these portions. In addition, the inner portion 119a includes piece members 111 to 114 and connection portions 130 each of which allows the relative positional relationship between adjacent piece members to be changed. The outer portion 119 includes piece members 115 to 118 and connection portions 130 each of which allows the relative positional relationship between adjacent piece members to be changed.

Each of the piece members 112 to 114 is formed in such a manner that a circular annular recess 121a is provided as a holding portion on one of flat surfaces of a plate-shaped plane member 120a. In addition, a side surface opening is provided in the plane member 120a so as to be connected from an outer peripheral side surface of the plane member 120a to the recess 121a such that the recesses 121a of the adjacent piece members are connected to each other. As shown in FIG. 20, the side surface opening is provided at two locations on a horizontal axis 124 passing through a center 123 of each of piece members 112 to 114. This side surface opening allows the primary coil to be stably arranged on each piece member. The plane member 120a has a shape obtained by cutting a circular plate along a plane orthogonal to the horizontal axis 124.

The piece member 111 has the substantially same structure as the piece members 112 to 114 but is different therefrom in that the piece member 111 is provided with an extension portion for fixing a female portion 134 which forms the connection portion 140, onto the flat surface at the side at which the recess 121a is provided. A recess 121a and a side surface opening are also provided in the extension portion.

Each of the connection portions 130 that connect the piece members 111 to 114 is composed of a hinge similarly to the first embodiment and other embodiments. The connection portions 130 are provided at two locations between the adjacent plane members 120a with the side surface openings interposed between the two locations. In addition, each connection portion 130 includes a first female portion 130a, a second female portion 130b, and a male shaft portion that is fitted into through holes provided in both female portions 130a and 130b. Each of the first female portion 130a and the second female portion 130b only needs to be fixed to any of the adjacent piece members. For example, the first female portion 130a can be provided at the piece member 114, and the second female portion 130b can be provided at the piece member 113.

A fixing portion for preventing the primary coil from falling off of the recess may be provided at each of the piece members 112 to 114. Examples of such a fixing portion include a structure provided so as to cover at least a part of the opening formed at the recess 121a.

Each of the piece members 115 to 118 is formed in such a manner that a circular recess 121 is provided as a holding portion on one of flat surfaces of an annular plane member 120 having a through hole 122. The piece member 115 and the piece members 116 to 118 respectively have the same structures as the piece member 111 and the piece members 112 to 114, except that each of the piece member 115 and the piece members 116 to 118 has the through hole 122. The piece member 115 and the piece members 116 to 118 are connected to each other by similar connection portions 130. In the present embodiment, the piece members 111 to 114 which form the inner portion 119a, are smaller in size than the piece members 115 to 118 which form the outer portion 119. A fixing portion for preventing the primary coil from falling off of the recess may also be provided at each of the piece members 115 to 118. Examples of such a fixing portion include a structure provided to cover at least a part of the opening formed at the recess 121.

The numbers of the piece members that form the inner portion 119a and the outer portion 119 can be determined as appropriate in accordance with the three-dimensional arrangement of a desired primary coil, and the number of the piece members of the inner portion 119a and the number of the piece members of the outer portion 119 may be different from each other or may be equal to each other. The structure of the inner portion 119a and the outer portion 119 in the assembled state can be determined as appropriate in accordance with the three-dimensional arrangement of the desired primary coil. Examples of the structure include a triangular tubular structure, a square tubular structure, and a polygonal tubular structure having five or more sides The recesses 121 and 121a which are the holding portions are provided on the piece members 111 to 118 which form the transformable member, in a manner of facing the same side in the unfolded state. The holding portions are provided as described above, thereby easily arranging the primary coil on the holding portions in the unfolded state. In addition to the annular recess, a helical or scroll-shaped recess may be provided on each piece member. Moreover, when a helical recess is provided, the piece member may be formed in, for example, a cone shape, a truncated cone shape, or the like, and the recess may be provided on an inclined surface of the piece member.

The intermediate portion 140 includes (i) female portions 134 and 135 that are fixed to the piece members 111 and 115, (ii) an intermediate shaft portion 141 that connects the inner portion 119a and the outer portion 119 with a predetermined interval provided therebetween, and (iii) male shaft portions that are fitted into through holes provided in the female portions 134 and 135 and female portions 142 and 143 of the intermediate shaft portion 141. The intermediate shaft portion 141 has: an elongated shaft portion 146 having a portion formed in a crank shape; and female portions 52 and 53 provided at both ends of the shaft portion 146. Through holes are provided in the female portions 52 and 53. The female portions 134 and 135 are rotated relative to the intermediate shaft portion 141 about the individual rotation centers that are the respective central axes in the longitudinal direction of the male shaft portions, thereby changing the relative positional relationship between the piece member 111 and the piece member 115 while the inner portion 119a and the outer portion 119 are connected to each other. In the present embodiment, the shaft portion 146 has the portion formed in the crank shape, but the shape of the shaft portion 146 can be changed as appropriate in accordance with the structure of each piece member, the manner of transforming the transformable member, and the like.

Hereinafter, the case of transforming the mold 100 from the unfolded state into the assembled state will be described.

First, the piece members 112 to 114 to which the female portions 130a or 130b of the connection portions 130 are fixed are moved in the direction of an arrow (counterclockwise) in FIG. 21 about the individual rotation centers that are the respective connection portions 130 in the inner portion 119a, thereby transforming the inner portion 119a that is in a straight shape in the unfolded state into a square tubular shape. Accordingly, the inner portion 119a is made into the assembled state. In addition, the intermediate shaft portion 141 is moved in the direction of an arrow (counterclockwise) in FIG. 21 about the female portion 134 (female portion 143) of the intermediate portion 140, and the piece members 115 to 118 to which the female portions 130a or 130b of the connection portions 130 are fixed are moved in the direction of an arrow (counterclockwise) in FIG. 21 about the individual rotation centers that are the respective connection portions 130 in the outer portion 119. With this, the outer portion 119 that is in a straight shape in the unfolded state is transformed into a square tubular shape. Accordingly, the outer portion 119 is made into the assembled state. At this time, as shown in FIG. 22, the vicinity of the connection portion between the piece member 111 and the piece member 112 is located within the through hole 122 of the piece member 115, the vicinity of the connection portion between the piece member 112 and the piece member 113 is located within the through hole 122 of the piece member 116, the vicinity of the connection portion between the piece member 113 and the piece member 114 is located within the through hole 122 of the piece member 117, and the side of the piece member 111 at which the female portion 134 is fixed and the side of the piece member 114 at which the connection portion 130 is not provided are partially located within the through hole 122 of the piece member 118. As described above, in the present embodiment, in the assembled state, the respective piece members 111 to 114 which form the inner portion 119a, and the connection portions 130 and 140 are partially located within the through holes 122 of the respective piece members 115 to 118 which form the outer portion 119.

In addition, in the present embodiment, the mold 100 is configured in such a manner that, in the assembled state, the recesses 121a which are the holding portions formed in the piece members 111 to 114 forming the inner portion 119a, face the outer side of the inner portion 119a, and the recesses 121 which are the holding portions formed in the piece members 115 to 118 forming the outer portion 119, face the inner side of the outer portion 119.

In one or more embodiments of the present invention, a production diagram for an in-vivo indwelling member can be imaged by using the above-described mold.

In addition, in one or more embodiments of the present invention, an in-vivo indwelling member can be produced by using the above-described mold, for example. Hereinafter, embodiments will be described regarding the mold 10a shown in FIG. 23 according to the modification of the first embodiment, and the mold 70 according to the third embodiment.

A method for producing an in-vivo indwelling member when the mold 10a according to the modification of the first embodiment is used will be described.

First, the mold 10a is made into the unfolded state in which the piece members 11 to 18 are straight as shown in FIG. 23. Then, a primary coil 1 having a predetermined length as shown in FIG. 1 is prepared, for example, and arranged on the recesses 21, 21a, 81, 82, and 83, which are the holding portions of the piece members 11 to 18. In the example shown in FIG. 23, one end of the primary coil is arranged along the upper portion, in FIG. 23, of the recess 81 from the vicinity of the female portion 36b at a piece member 12a, or arranged along the recesses 82 and 83 of the piece member 12a (see a broken line portion in FIG. 23). Thereafter, the primary coil is arranged on the recesses 21a, 81, 82, and 83 which are the holding portions of the piece members 11 to 14 of the inner portion 19a, in the order of the lower portion in FIG. 23, of the recess 21a of the piece member 13, the upper portion in FIG. 23, of the recess 21a of the piece member 14, the lower portion thereof, the upper portion in FIG. 23, of the recess 21a of the piece member 13, the lower portion in FIG. 23, of the recess 81 of the piece member 12a, and the upper portion in FIG. 23, of the recess 21a of the piece member 11. In FIG. 23, the portions of the primary coil that are arranged on the piece members 11, 12a, 13, and 14 are shown by reference characters e, f, g, and h, respectively.

Subsequently, the primary coil is arranged on the recesses 21 which are the holding portions of the piece members 15 to 18 of the outer portion 19, in the order of the lower portion in FIG. 23, of the recess 21 of the piece member 15, the upper portion in FIG. 23, of the recess 21 of the piece member 16, the lower portion in FIG. 23, of the recess 21 of the piece member 17, the upper portion in FIG. 23, of the recess 21 of the piece member 18, the lower portion thereof, the upper portion in FIG. 23, of the recess 21 of the piece member 17, and the lower portion in FIG. 23, of the recess 21 of the piece member 16. The other end of the primary coil is located in the vicinity of the connection portion 30 between the piece member 16 and the piece member 15. In FIG. 23, the portions of the primary coil that are arranged on the piece members 15, 16, 17, and 18 are shown by reference characters E, F, G, and H, respectively. The portion of the primary coil corresponding to the continuous portion between the inner portion 19a (piece member 11) and the outer portion 19 (piece member 15) is shown by reference character I.

According to one or more embodiments of the present invention, the primary coil on the holding portions of the respective piece members is thus arranged only once, thereby molding an in-vivo indwelling member having a secondary shape with a complicated three-dimensional arrangement different from a conventional helical shape. This eliminates necessity of winding of the primary coil around a core as in the conventional art. Accordingly, damage of the primary coil by a winding process can be reduced. In addition, it is only necessary to arrange the primary coil on the piece members alternately and sequentially at the upper side and the lower side in FIG. 23. This reduces the possibility of winding in the wrong order as in the conventional case in which a core or the like is used, thereby further improving the workability. As a result, the imparted secondary shape becomes stable, and mass production of in-vivo indwelling members having stable quality can be easily carried out, so that the production method is excellent in mass productivity and quality control.

After the primary coil is thus arranged on the mold 10a in the unfolded state, the primary coil is fixed by fixing portions depending on the necessity, and the mold 10a is transformed so that the inner portion 19a is arranged at the inner side of the outer portion 19 of the mold 10a, similarly as shown in FIGS. 8 and 9, with the primary coil being arranged on the mold 10a. Thus, the mold 10a is made into the assembled state.

The mold 10a is transformed into the assembled state with the primary coil being arranged thereon as described above, thereby transforming the primary coil 1 into a secondary shape with a three-dimensional arrangement. This means that a secondary shape can be imparted to the primary coil in accordance with the arrangement of the piece members 11 to 18 of the mold 10a in the assembled state, and the arrangement of the primary coil onto the recesses 21, 21a, 81, 82, and 83 which are the holding portions provided in the piece members 11 to 18.

Transformation of the mold from the unfolded state into the assembled state may be performed manually by an operator, or may be performed by an in-vivo indwelling member production apparatus having the above-described mold.

After the mold is thus transformed into the assembled state with the primary coil arranged thereon, heat treatment is further performed to cause the primary coil arranged on the mold to memorize and fix the secondary shape with the three-dimensional arrangement. The heat treatment can be performed by using a heating furnace such as an atmospheric furnace, a light condensing furnace, and a vacuum furnace. The heating temperature may be determined as appropriate in consideration of the material used for the primary coil, or others. When a metal material is used, the heating temperature may be 400 to 900° C., such as 550 to 750° C. for effective fixation of the secondary shape. In addition, the heating time may be determined as appropriate in consideration of the material used for the primary coil, or others. When a metal material is used, the heating time may not be shorter than 30 minutes for effective fixation of the secondary shape.

After the heat treatment is performed, the cooled mold is made into the unfolded state, and the primary coil is taken out from the mold. Thus, an in-vivo indwelling member (secondary coil) having the memorized secondary shape with the three-dimensional arrangement is obtained.

Figure 24A:
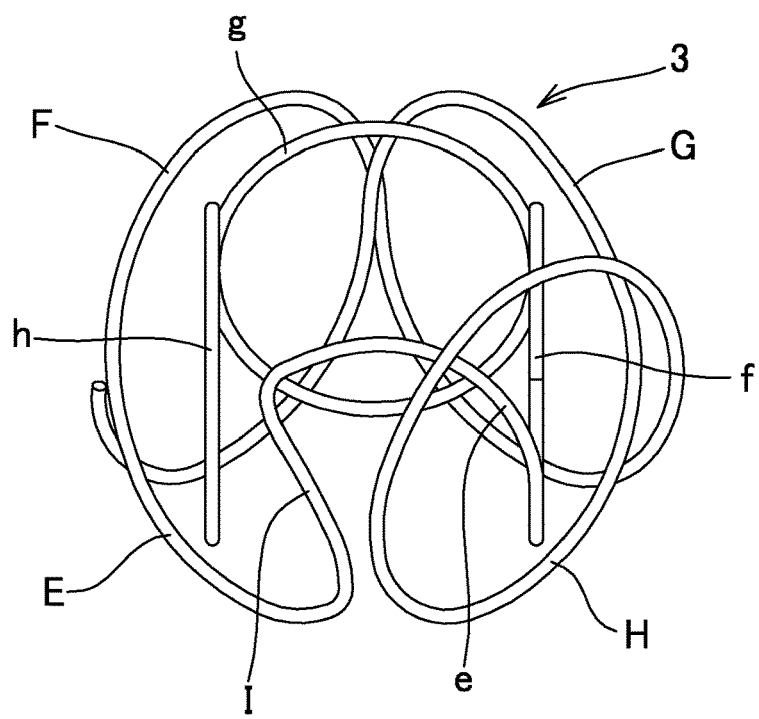
FIG. 24A is a perspective view schematically showing an example of the in-vivo indwelling member produced by using the modification of the first embodiment of the mold according to one or more embodiments of the present invention.
Figure 24B:
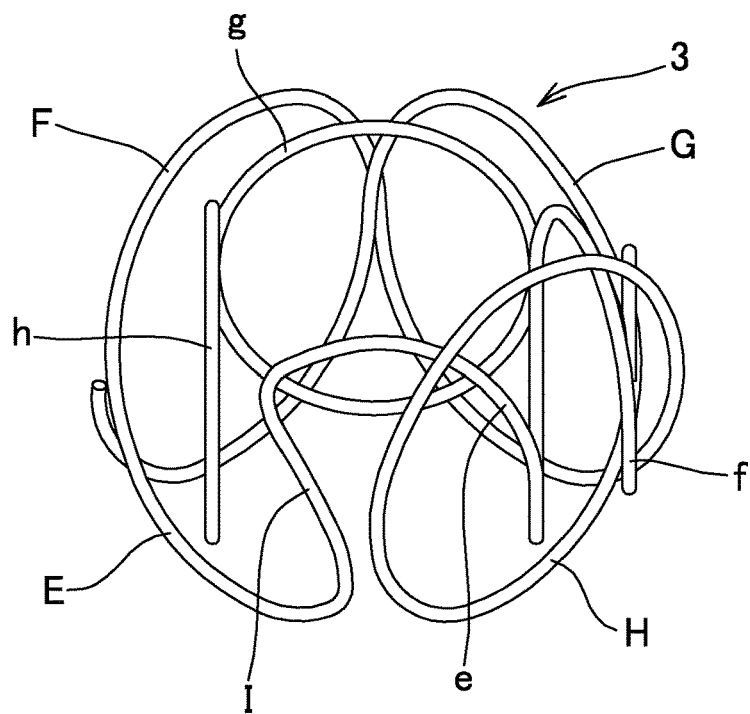
FIG. 24B is a perspective view schematically showing another example of the in-vivo indwelling member produced by using the modification of the first embodiment of the mold according to one or more embodiments of the present invention.

When the one end of the primary coil is arranged along the upper portion, in FIG. 23, of the recess 81 from the vicinity of the female portion 36b at the piece member 12a as described above, an in-vivo indwelling member 3 is obtained in which the portions of the primary coil that are shown by e to h and E to H and respectively arranged on the piece members 11 to 18 as shown in FIG. 23 define a secondary shape with a three-dimensional arrangement as shown in FIG. 24(a). In addition, when the one end of the primary coil is arranged along the recesses 82 and 83 of the piece member 12a (see the broken line portion in FIG. 23), an in-vivo indwelling member 4 is obtained in which the portions of the primary coil that are shown by e to h and E to H (including the portion shown by I, which is the continuous portion between the portions shown by e and E) and respectively arranged on the piece members 11 to 18 as shown in FIG. 23 define a secondary shape with a three-dimensional arrangement as shown in FIG. 24(b). Moreover, since the primary coil is arranged on the recesses along the recesses which are the holding portions, only once as shown in FIG. 23, the primary coil can be easily taken out from the mold.

A method for producing an in-vivo indwelling member when the mold 60 of the third embodiment is used will be described.

First, the mold 70 is made into the unfolded state in which the piece members 71 to 74 of the inner portion 79a and the piece members 75 to 78 of the outer portion 79 are respectively straight as shown in FIG. 25. At this time, the angle formed between the inner portion 79a and the outer portion 79 can be changed as appropriate in accordance with an operation of arranging a primary coil on the recesses. Then, a primary coil 1 having a predetermined length as shown in FIG. 1 is prepared, for example, and arranged on the recesses 21, 21a, 81, 82, and 83, which are the holding portions of the piece members 71 to 78. In the example shown in FIG. 25, one end of the primary coil is arranged along the recesses 82 and 83 of the piece member 72. Thereafter, the primary coil is arranged on the recesses 21a, 81, 82, and 83 which are the holding portions of the piece members 71 to 74 of the inner portion 79a, in the order of the lower portion in FIG. 25, of the recess 21a of the piece member 73, the upper portion in FIG. 25, of the recess 21a of the piece member 74, the lower portion thereof, the upper portion in FIG. 25, of the recess 21a of the piece member 73, the lower portion in FIG. 25, of the recess 81 of the piece member 72, and the upper portion in FIG. 25, of the recess 21a of the piece member 71. In FIG. 25, the portions of the primary coil that are arranged on the piece members 71, 72, 73, and 74 are shown by reference characters e, f, g, and h, respectively.

Subsequently, the primary coil is arranged on the recesses 21 which are the holding portions of the piece members 75 to 78 of the outer portion 79, in the order of the lower portion in FIG. 25, of the recess 21 of the piece member 75, the upper side thereof, the lower portion in FIG. 25, of the recess 21 of the piece member 76, the upper portion in FIG. 25, of the recess 21 of the piece member 77, the lower portion in FIG. 25, of the recess 21 of the piece member 78, the upper portion thereof, the lower portion in FIG. 25, of the recess 21 of the piece member 77, and the upper portion in FIG. 25, of the recess 21 of the piece member 76. The other end of the primary coil is located in the vicinity of the upper most portion of the piece member 76 in the upper side of FIG. 25. In FIG. 25, the portions of the primary coil that are arranged on the piece members 75, 76, 77, and 78 are shown by reference characters E, F, G, and H, respectively. The portion of the primary coil corresponding to the continuous portion between the inner portion 79a (piece member 71) and the outer portion 79 (piece member 75) is shown by reference character 1.

Even when the mold 70 of the third embodiment is used, an in-vivo indwelling member having a secondary shape with a complicated three-dimensional arrangement different from a conventional helical shape can be molded by arranging the primary coil on the holding portions of the respective piece members only once as described above. In addition, it is only necessary to arrange the primary coil on the piece members alternately and sequentially at the upper side and the lower side in FIG. 25. Therefore, the same advantageous effects as in the case of using the mold according to the first embodiment (including the modification) can be expected.

After the primary coil is thus arranged on the mold 70 in the unfolded state the primary coil is fixed by fixing portions depending on the necessity, and the mold 70 is transformed, with the primary coil being arranged thereon, so that the inner portion 79a is arranged at the inner side of the outer portion 79 of the mold 70, similarly as shown in FIGS. 18 and 19. Thus, the mold 70 is made into the assembled state.

The mold 70 is thus transformed into the assembled state with the primary coil being arranged thereon, thereby transforming the primary coil 1 into a secondary shape with a three-dimensional arrangement. This means that a secondary shape can be imparted to the primary coil in accordance with the arrangement of the piece members 71 to 78 of the mold 70 in the assembled state, and the arrangement of the primary coil onto the recesses 21, 21a, 81, 82, and 83 which are the holding portions provided in the piece members 71 to 78.

Transformation of the mold from the unfolded state into the assembled state may be performed manually by an operator, or may be performed by an in-vivo indwelling member production apparatus having the above-described mold.

Figure 26:
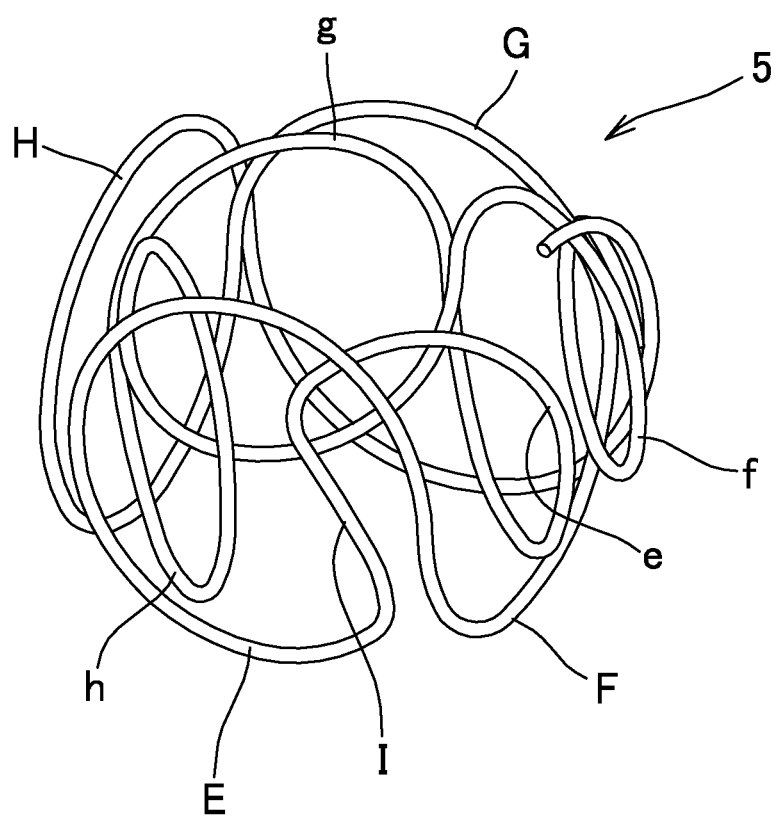
FIG. 26 is a perspective view schematically showing an example of the in-vivo indwelling member produced by using the modification of the third embodiment of the mold according to one or more embodiments of the present invention.
Figure 27:
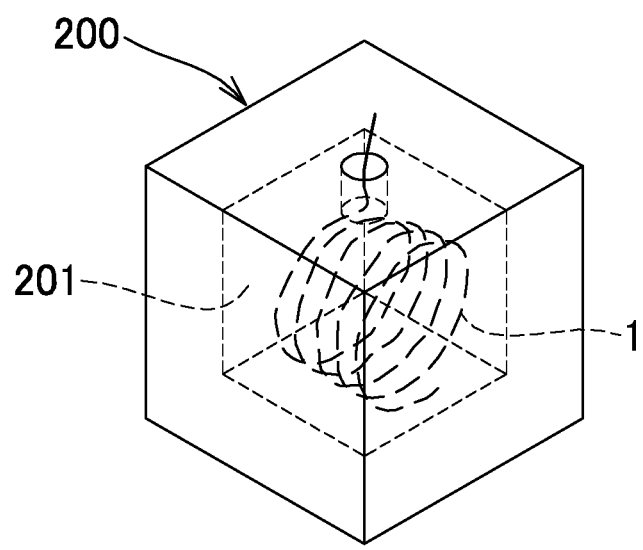
FIG. 27 is a perspective view schematically showing a state when a primary coil is inserted into a conventional mold.

After the mold 70 is thus transformed into the assembled state with the primary coil being arranged thereon, similarly to the case of the modification of the first embodiment, heat treatment and cooling treatment are further performed to obtain an in-vivo indwelling member 5 in which the primary coil 1 arranged on the mold 70 is caused to memorize a secondary shape with a three-dimensional arrangement (see FIG. 26). The in-vivo indwelling member 5 is obtained in which the portions of the primary coil that are shown by e to h and E to H (including the portion shown by I, which is the continuous portion between the portions shown by e and E) and respectively arranged on the piece members 71 to 78 as shown in FIG. 25 define a secondary shape with a three-dimensional arrangement as shown in FIG. 26.

The in-vivo indwelling member obtained as described above can be suitably used as an embolus material to be used in treating a bulge such as an aneurysm formed in a blood vessel. Particularly, in the case of an embolus material obtained by using the mold having the transformable member that forms a space surrounded by the inner portion and the outer portion, the embolus material has a secondary shape with a three-dimensional arrangement that can correspond to the shape of the inner wall surface of the aneurysm, while ensuring a space within the bulge, even when the bulge is a wide-neck aneurysm. With this, the embolus material is firmly and stably fixed within the bulge by applying pressing force to the inner wall surface of the bulge, and also a space corresponding to the space of the transformable member can be formed. As a result, another coil for filling the space can be easily inserted. Therefore, the embolus material obtained by using the mold having the transformable member that forms a space surrounded by the inner portion and the outer portion is useful as an embolus material that serves as a frame for inserting another coil.

DESCRIPTION OF THE REFERENCE CHARACTERS

1, 1a, 1b primary coil
2 wire
3, 4, 5 in-vivo indwelling member
10, 10a, 60, 70, 100, 200 mold
11, 12, 12a, 13, 14, 15, 16, 17, 18 piece member
19, 79, 119 outer portion
19a, 79a, 119a inner portion
20, 20a loop member
21, 21a, 81, 82, 83, 121, 121a holding portion (recess)
22, 22a, 33, 39, 44, 45, 54, 55, 122 through hole
23, 86, 123 center
24, 85, 124 horizontal axis
25 fixing portion (hollow tube)
26 hinge structure
27, 28 member
30, 34, 35, 130 connection portion
30a, 30b, 36a, 36b, 42, 43, 52, 53, 134, 135 female portion
31, 37 fitting portion
32, 38 fixing portion
40, 50, 90, 140 connection portion (intermediate portion)
41, 51, 141 intermediate shaft portion
46, 56, 146 shaft portion
71, 72, 73, 74, 75, 76, 77, 78 piece member
80 member
84 inclined surface
111, 112, 113, 114, 115, 116, 117, 118 piece member
120, 120a plane member
130a first female portion
130b second female portion
142, 143 female portion

The invention claimed is:

1. A mold for use in producing an in-vivo indwelling member having a primary coil formed in a three-dimensional shape, the mold comprising:
   a plurality of ring shaped members, each having a holding portion for holding the primary coil, the plurality of ring shaped members connected to form a transformable member transformable between an assembled state and an unfolded state, wherein
   each of the ring shaped members has a recessed portion along a circumference of the ring shaped member, as the holding portion, so that the primary coil can be held on the recessed portion, and
   the transformable member has, in the assembled state, an outer portion that is arranged at an outer side and an inner portion that is arranged at an inner side of the outer portion with being connected to the outer portion.

2. The mold according to claim 1, wherein the plurality of ring shaped members are connected to each other by a connection portion that allows a relative positional relationship between adjacent piece members to be changed.

3. The mold according claim 1 or 2, further comprising at least one member that has a spiral or helical shaped holding portion for holding the primary coil.

4. The mold according to claim 1, wherein the plurality of ring shaped members are connected so that the transformable member can be linear in the unfolded state.

5. The mold according to claim 1, wherein
   the inner portion is partially located within at least one of ring holes of the ring-shaped members forming the outer portion in the assembled state.

6. The mold according to claim 1, wherein each holding portion is provided at a peripheral portion of the transformable member.

7. The mold according to claim 1, wherein the plurality of ring shaped members are arranged so that the holding portions are aligned in the same side of the transformable member in the unfolded state.

8. A method for producing an in-vivo indwelling member having a primary coil formed in a three-dimensional shape, the method comprising the steps of:

providing the mold of claim 1, arranging the primary coil on the mold that is in an unfolded state; and transforming the primary coil into a three-dimensional shape by transforming the mold with the primary coil arranged thereon so that the inner portion of the mold is arranged at the inner side of the outer portion of the mold, thereby making the mold into the assembled state.

9. The mold according to claim 1, wherein each of the plurality of ring shaped members has on an outer peripheral surface the recessed portion as the holding portion for holding the primary coil.

* * * * *